United States Patent
Motzer

(10) Patent No.: US 6,301,512 B1
(45) Date of Patent: Oct. 9, 2001

(54) ULTRASONIC DATA ANALYSIS AND DISPLAY SYSTEM

(75) Inventor: William P. Motzer, Seattle, WA (US)

(73) Assignee: The Boeing Company, Seattle, WA (US)

(*) Notice: Subject to any disclaimer, the term of this patent is extended or adjusted under 35 U.S.C. 154(b) by 1335 days.

(21) Appl. No.: 08/632,638

(22) Filed: Apr. 15, 1996

Related U.S. Application Data

(63) Continuation of application No. 08/176,035, filed on Dec. 30, 1993, now abandoned.

(51) Int. Cl.[7] .................................................. G06F 17/00
(52) U.S. Cl. .............................. 700/90; 345/115; 702/39
(58) Field of Search ........................... 345/115; 364/507, 364/508, 550; 700/90; 702/35, 36, 39

(56) References Cited

U.S. PATENT DOCUMENTS

| | | | |
|---|---|---|---|
| 3,977,236 | * 8/1976 | Raatz, Jr. et al. | 73/614 |
| 4,097,835 | 6/1978 | Green | 340/1 R |
| 4,104,725 | * 8/1978 | Rose et al. | 364/487 |
| 4,141,347 | 2/1979 | Green et al. | 128/2 V |
| 4,176,658 | 12/1979 | Kossoff et al. | 128/660 |
| 4,303,885 | * 12/1981 | Davis et al. | 324/237 |
| 4,342,029 | 7/1982 | Hofmanis et al. | 345/22 |
| 4,395,707 | * 7/1983 | Satrapa | 345/180 |
| 4,398,540 | 8/1983 | Takemura et al. | 126/660 |
| 4,471,348 | * 9/1984 | London et al. | 364/550 X |
| 4,476,874 | 10/1984 | Taenzer et al. | 126/663 |
| 4,501,277 | 2/1985 | Hongo | 128/660 |
| 4,589,284 | * 5/1986 | Breimesser et al. | 73/626 |
| 4,779,623 | 10/1988 | Sumino et al. | 128/660.04 |
| 5,005,418 | 4/1991 | Anderson | 73/625 |
| 5,049,738 | * 9/1991 | Gergely et al. | 250/301 |
| 5,282,213 | * 1/1994 | Leigh et al. | 364/487 X |
| 5,539,426 | * 7/1996 | Nishikawa et al. | 345/115 |

FOREIGN PATENT DOCUMENTS

| | | | |
|---|---|---|---|
| 0476495-A1 | * 3/1992 | (EP). | |
| 2000-139915-A | * 5/2000 | (JP). | |

OTHER PUBLICATIONS

Beach et al: "Pseudocolo B–mode arterial images to quantify echogenicity of atherosclerotic plaque"; Ultrasound in Medicine & Biology, 1994, vol. 20, No. 8, pp. 731–742, (Abstract Only).*

"A Real Time Ultrasonic Diagnostic System for Simultaneous Image Display," *JEE*, vol. 16, No. 154:66–69 (Oct. 1979).

* cited by examiner

*Primary Examiner*—Edward R. Cosimano
(74) *Attorney, Agent, or Firm*—Christensen O'Connor Johnson Kindness PLLC

(57) ABSTRACT

An ultrasonic data analysis and display system for use with ultrasonic test apparatus. The ultrasonic analysis and display system includes a display that is divided into six different display formats, including a pulse echo, a time of flight display, an A-Scan, a horizontal and vertical B-Scan, and a control display. Each of the displays gives a different view of the ultrasonic test data obtained from a test part. When a portion of the ultrasonic data in any of the display formats is selected, the other display formats are automatically updated to reflect the operator's selections. The format of the displayed data can be changed to a half-wave positive, a half-wave negative, or a full-wave rectification. Distances within any of the display formats can be measured by selecting two data points. Also, different color palettes for displaying the ultrasonic data can be selected, and portions of the ultrasonic data displayed in the pulse echo or time of flight displays can be enlarged by zooming in on a selected portion.

40 Claims, 16 Drawing Sheets

ULTRASONIC DATA ANALYSIS AND DISPLAY SYSTEM

This application is a continuation application based on prior application Ser. No. 08/176,035, filed on Dec. 30, 1993 abandoned.

FIELD OF THE INVENTION

The present invention relates to systems and apparatus for displaying and analyzing data obtained from an ultrasonic scan of an object.

BACKGROUND OF THE INVENTION

As new materials, such as composite materials, are used in more applications throughout the aircraft and other industries, the use of nondestructive test equipment, such as ultrasonic test equipment, to inspect fabricated parts prior to use has become widespread. Ultrasonic test equipment allows an operator to nondestructively inspect the interior of parts, such as a wing or control surface panel, for flaws and other areas of discontinuity such as delaminations, foreign objects introduced during fabrication, etc.

Ultrasonic test equipment works by generating a high frequency sound wave at an ultrasonic transducer located near the surface of the part being tested. The ultrasonic transducer is oriented such that the high frequency sound wave travels through the part, usually in the height or thickness direction. When the sound wave contacts a discontinuity, such as a flaw, delamnination, or a change in the stiffness of the material, part of the sound energy is reflected. The reflected sound energy travels back through the part and is received by the same ultrasonic transducer, which acts as both a transmitter and receiver in what is commonly referred to as a "pulse echo" ultrasonic test system. Alternatively, the high frequency sound wave generated by the ultrasonic transmitter passes through the entire thickness of the part and is received on the opposite side of the part by a separate receiver in what is commonly known as "through transmission" ultrasonic testing. Pulse echo ultrasonic testing is the most common technique in use because access to only one side of a part is required. While useful with through transmission ultrasonic testing apparatus, as will be better understood from the following description, the present invention was developed for use with pulse echo ultrasonic testing apparatus.

The waveform of the received RF signal from an ultrasonic test is recorded by the test equipment and/or displayed on a monitor or other display device. The data contained in the RF signal can be displayed in a number of different formats. The most commonly used display format is called a "pulse echo." A pulse echo is basically a top down view of the portion of the part that has been ultrasonically tested. A pulse echo gives the operator a general idea of the size and shape of any discontinuities within the part in the height or thickness direction.

Alternatively, the ultrasonic data may be displayed in the form of an A-Scan, a B-Scan, or a time of flight display. A B-Scan displays the ultrasonic data in a way that graphically portrays the cross section through the thickness of the test part while an A-Scan is simply the RF signal plotted as a graph of time versus amplitude of the signal. A time of flight display is the ultrasonic data displayed in a way that shows a top down view of the area scanned graphically portraying the distance into the part to the point where a discontinuity is located.

Prior art ultrasonic test equipment generally displays a real time continuous A-Scan as the ultrasonic transducer moves along the part and also records the data used to produce a pulse echo. During scanning or after testing, the pulse echo is typically output as a hard copy to be saved for later reference. Generally, the entire RF signal is not recorded by the test equipment, thus once a scan is complete, a test must be reperformed if any additional information is desired. Prior art systems do not allow an operator to simultaneously view the B-Scan, pulse echo, A-Scan or time of flight display to get a better understanding of the ultrasonic data. Nor do prior art ultrasonic test systems allow the operator to view a display of the ultrasonic data, select a portion of the data that is particularly relevant, and create other displays based upon the operator's selections.

Typically, in the past, a user will examine the B-Scan or pulse echo during testing in an attempt to locate flaws. If a flaw is located, the user will reprogram the test equipment to obtain additional test data in the area where a flaw is observed. It is not uncommon for a user to perform and observe a B-Scan display during testing and once a flaw is located, repeat the test while observing a pulse echo display and then repeat the test again observing an A-Scan or time of flight display to obtain a better understanding of the test results. Obviously, this approach is very time consuming and, thus, undesirably expensive.

One goal of the ultrasonic analysis and display system of the present invention is to allow a user to simultaneously view ultrasonic test data in a number of different display formats and to manipulate the displays in order to rapidly and quickly obtain a better understanding of the data while eliminating some of the problems present in the prior art.

SUMMARY OF THE INVENTION

The present invention provides an operator with a sophisticated analysis tool for analyzing ultrasonic test data obtained from an ultrasonic test of a part. The invention allows the operator to display the ultrasonic test data simultaneously on a computer display in a number of different display formats, including pulse echo, time of flight display, A-Scan, and horizontal and vertical B-Scans.

The present invention is implemented in the form of a computer system that includes a display, input means responsive to an operator's input, a processor for altering the display, and memory means for storing data and one or more programs for controlling the operation of the processor and, thus, the display. As a part being tested is scanned, the entire ultrasonic RF waveform is digitized and recorded for each point at which ultrasonic test data is taken. As a result, all of the ultrasonic test data is available for subsequent analysis as opposed to prior art systems where only portions of the test data or a hard copy of a single display format is kept for later analysis.

The invention provides a user interface for displaying and analyzing the ultrasonic test data. The user interface simultaneously displays the ultrasonic test data in the form of an A-Scan in one portion of the display, and in the form of a pulse echo in another portion of the display. The invention allows an operator to select a portion of the ultrasonic test data displayed in either the A-Scan or the pulse echo for updating. When this occurs, the program causes the processor to automatically update the other portions of the display to correspond to the operator's selection.

In accordance with other aspects of the invention, the user interface also displays a first B-Scan along one axis of the test part in one portion of the display and a second B-Scan along a second axis of the test part in another portion of the display.

In accordance with still other aspects of this invention, the ultrasonic test data is displayed in the form of a time of flight display in yet another portion of the display.

In accordance with the invention, an operator may select a portion of the ultrasonic data displayed in any of the display formats and the processor will automatically update the other display formats. For example, in one form of the invention, the operator may select a data point in the pulse echo using horizontal and vertical cross hairs. A vertical B-Scan corresponding to the location of the vertical cross hair and a horizontal B-Scan corresponding to the location of the horizontal cross hair are then displayed. The operator may also select two data points in any of the displays and the distance between the two data points with respect to each other will be displayed.

In accordance with still further aspects of the invention, the pulse echo is displayed in the upper left corner of a computer display directly above the time of flight display. The A-Scan is displayed in the center of the display while a horizontal B-Scan is located in the upper right-hand corner directly above a vertical B-Scan. The operator may select data points within any of the displays and the other displays will be updated in response to the operator's selections.

As will be appreciated from the foregoing summary, the present invention provides an operator with an easy and effective data analysis tool. The operator may simultaneously view the ultrasonic test data in the various display formats thus allowing the operator to reach a more informed conclusion about the significance of the test data. In addition, the operator may examine any portion of the ultrasonic test data in more detail by simply selecting the desired data on any of the display formats.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF THE PREFERRED EMBODIMENT

Figure 1:
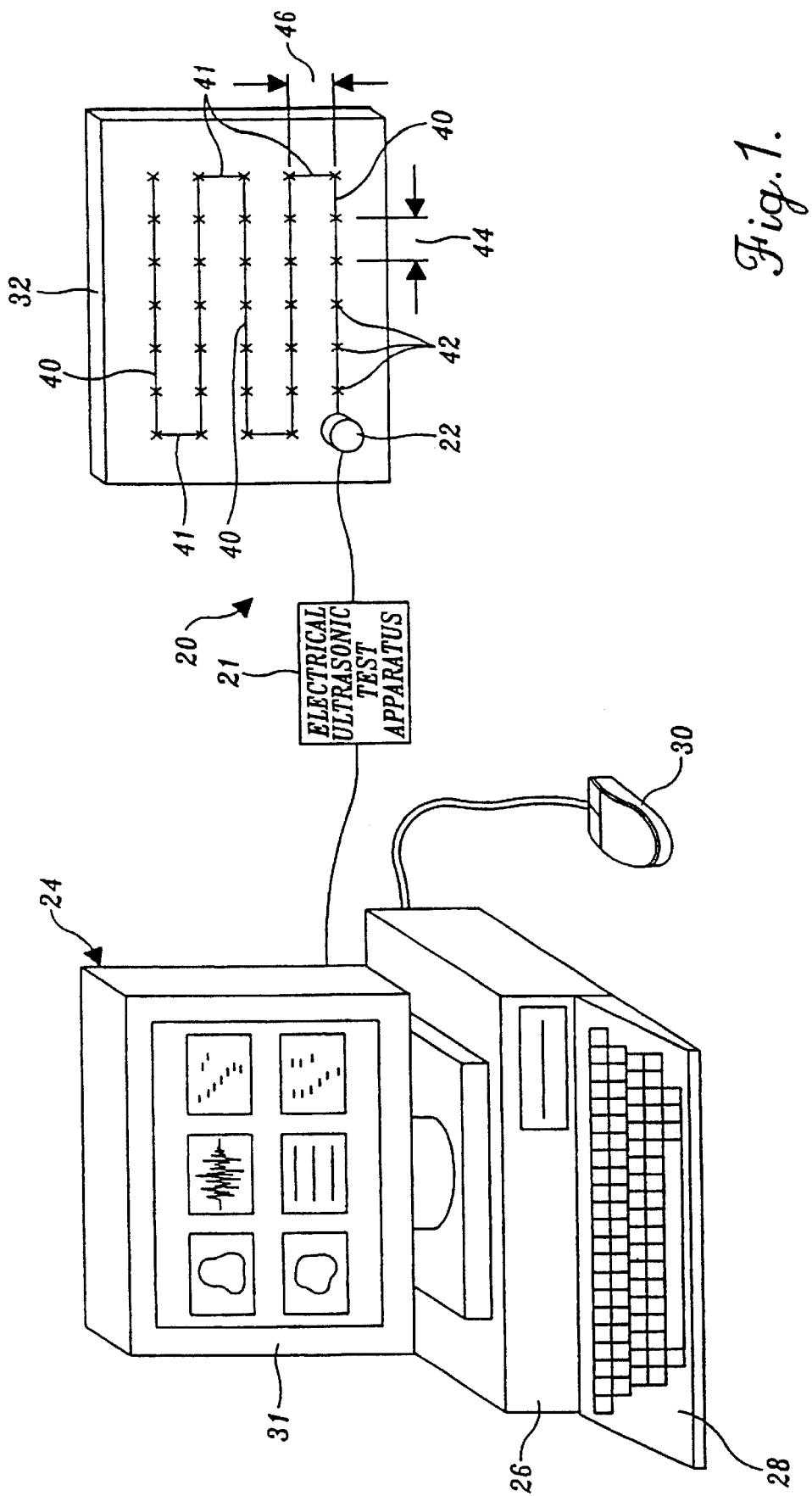
FIG. 1 is a schematic representation of an ultrasonic data acquisition, analysis and display system incorporating the present invention.

An apparatus for acquiring, analyzing and displaying ultrasonic test data is illustrated in FIG. 1. The acquisition portion of the apparatus (which does not form part of the present invention) comprises an ultrasonic test apparatus 20 that includes electrical and mechanical components shown as a block 21 and an ultrasonic transducer 22. The ultrasonic test apparatus 20 is connected to a computer system 24 that includes a central processing unit (CPU) 26, a display 31, and input devices, namely a keyboard 28 and a mouse 30.

The ultrasonic test apparatus 20 can take the form of any ultrasonic test equipment known to those skilled in the ultrasonic testing art capable of scanning different materials and parts for discontinuities including flaws or areas of delamination, etc. As is well known to those skilled in the ultrasonic test art, different types of industrial ultrasound tests are used to conduct through transmission ultrasound (TTU) and pulse echo (PE) ultrasound tests. In a TTU test, sound waves produced by an ultrasonic transmitter located on one side of the part and received by a receiver located on the opposite side of the part pass completely through the part. PE ultrasound test apparatus uses a single transducer located on one side of the part that functions as both a transmitter and a receiver. Pulse echo testing is preferred because access to only one side of the test part is required. In any event, ultrasonic test apparatus 20, in addition to one or more ultrasonic transducers 22, includes interface electronics and, usually, an electromechanical apparatus for moving the transducer(s) across the surface of the part to be tested. Frequently, the electromechanical scanning apparatus includes position sensors that monitor the position of the moving transducer.

In a pulse echo ultrasound apparatus, a high frequency sound wave generated by the ultrasonic transducer 22 enters a test part, such as a test part 32, at the location where test data is desired. As the high frequency sound wave passes through the thickness of the test part 32, the sound wave comes into contact with any areas of discontinuity located in the path of the beam. Such discontinuities could include a void or area of resin porosity, a delamination, foreign matter, or a change in stiffness caused by a composite ply formed of a different material, etc. When the high frequency sound wave contacts the discontinuity, a portion of the sound energy is reflected back through the part toward the ultrasonic transducer 22.

The ultrasonic transducer 22 is gated to act as both a transmitter that produces RF sound wave pulses and as a receiver that records the reflected RF sound wave signals. The time between when an RF pulse is transmitted and an RF reflection is received equals the time it took for the sound wave to pass into the test part, contact the area of discontinuity, and travel back to the ultrasonic transducer 22. Thus, the time between transmission and reception is related to the depth of the discontinuity. The amplitude of the RF signal is related to the magnitude of the discontinuity, as the larger the discontinuity, the more sound energy is reflected back towards the ultrasonic transducer 22.

In one actual embodiment of the invention, the ultrasonic transducer 22 is located on a mechanical arm (not shown) whose movement is precisely controlled by the computer 24. The mechanical arm moves the ultrasonic transducer 22 over the surface of the test part 32 in a precisely controlled raster scan during testing. An exemplary raster scan (enlarged for purposes of clarity) is shown by the lines 40 and 41 in FIG. 1. The mechanical arm moves the ultrasonic transducer 22 from a starting point in the lower left corner of the test part 32 to the lower right corner of the test part along line 40. As the ultrasonic transducer 22 moves across the test part, ultrasonic test data is taken at preprogrammed data points 42. While, typically, the data points 42 are equally spaced apart a distance 44, the computer 24 could be programmed to take data at irregular distances.

After moving across the width of the test part 32, the ultrasonic transducer indexes vertically upward a distance 46 along line 41. The ultrasonic transducer then moves backward across the width of the test part 32 taking ultrasonic test data at data points 42 as shown. The raster scan continues until the entire area of the test part 32 that is to be scanned is completed. Obviously, scanning patterns other than a raster scan pattern can be followed, if desired, depending on the shape of the part and other factors.

As the ultrasonic transducer 22 receives the reflected sound waves at an individual data point 42, the information is passed to the ultrasonic test apparatus 20 in the form of an RF signal. This RF signal is digitized by the ultrasonic test apparatus 20 or the computer 24 and the resulting digitized data is passed to and stored as a data array in a memory within the CPU 26. The location on the test part from which each set of digitized data originated can be determined by knowing the scan pattern and by knowing the position of the digitized data in the data array.

In one actual embodiment of the invention, each RF signal is digitized using 200 discrete data points. While the RF signal could be digitized using any number of data points, 200 data points were chosen due to the limitations of the display 31 used in this embodiment of the invention. The display 31 was a VGA display having a resolution of 640×480 pixels, using 16 colors. Each data point was represented by a single pixel, allowing the display to be divided into five separate display portions and a control portion, each portion having a resolution of slightly over 200×200 pixels. Thus, each of the five resulting display portions was capable of displaying the 200 separate data points in the form of a graph or other display format. The advantages of dividing the display into five separate display portions will be discussed in detail below.

Figure 2:
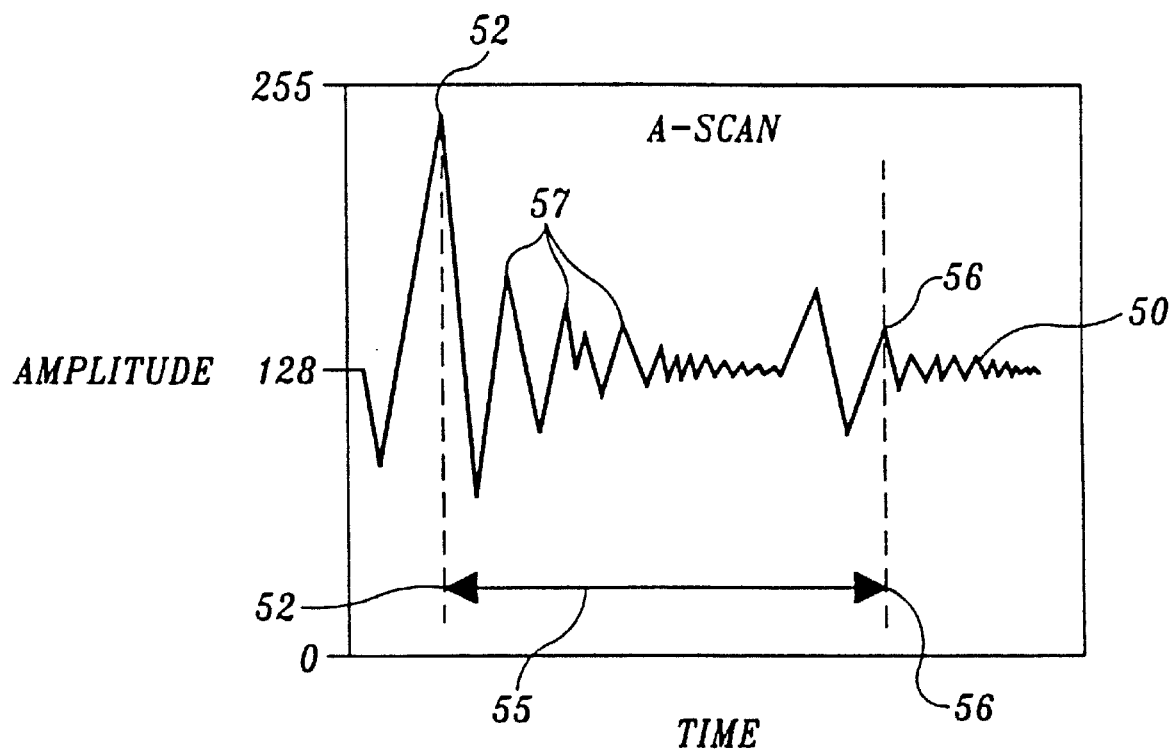
FIG. 2 is a graph of a representative A-Scan wherein time is plotted along the X-axis and amplitude is plotted along the Y-axis.

The digitized RF signal may be displayed as an "A-Scan," a representative example of which is illustrated in FIG. 2. An A-Scan is a graph of the reflected RF sound energy signal 50 received by the ultrasonic transducer 22 where time is plotted along the X-axis and amplitude is plotted along the Y-axis. In the actual embodiment of the invention referenced above, the RF signal 50 was digitized by assigning values from 0 to 255 to the amplitude of the RF signal, the value of 128 being assigned to zero volts.

As discussed above, the greater the discontinuity in the test part the greater the amplitude of sound energy reflected, thus the greater the amplitude of the RF signal. In the exemplary A-Scan shown in FIG. 2, the greatest amplitude reflection 52 is caused by the front surface of the test part 32. A smaller amplitude reflection 56 is caused by the back surface of the test part. Other reflections 57 shown in FIG. 2 represent discontinuities through the thickness of the test part 32 at the location where the ultrasonic data was taken. The reflections 57 could be voids, delaminations, other flaws within the test part, or could be the intersections between individual composite layers forming the test part.

It is possible to determine the thickness of the test part 32 or the distance between individual reflections 57 and thus the location of the discontinuities within the thickness of the test part using the information contained within an A-Scan. The time between reflections 57 of the A-Scan is determined from the graph of the RF sound energy signal 50. Knowledge of the time between reflections 57 and the speed of sound in the test part 32 allows the distance between reflections to be calculated by multiplying one-half the difference between the time between when an RF pulse is applied to the part as determined by the front surface reflection 50 and when a discontinuity reflection 57 is received by the speed of sound in the test part. As an example, if thickness of the test part 32 is desired, the time 55 between when the reflection 52 from the front surface of the test part was received is subtracted from the time 56 when the reflection 56 from the rear surface of the test part is first determined. The time is then halved and the result multiplied by the speed of sound in the test part.

To a skilled operator, an A-Scan provides a great deal of information about a test part 32. However, because an A-Scan represents test data through the thickness of the test part 32 at only a single location, it is difficult, if not impossible, for an operator to fully understand the internal structure of a test part solely from an A-Scan display. One goal of the present invention is to provide the operator with a more complete understanding of the internal structure of a part, particularly a part with flaws, by displaying ultrasonic test data in a number of different display formats and by allowing the operator to alter the display formats at will.

Figure 3:
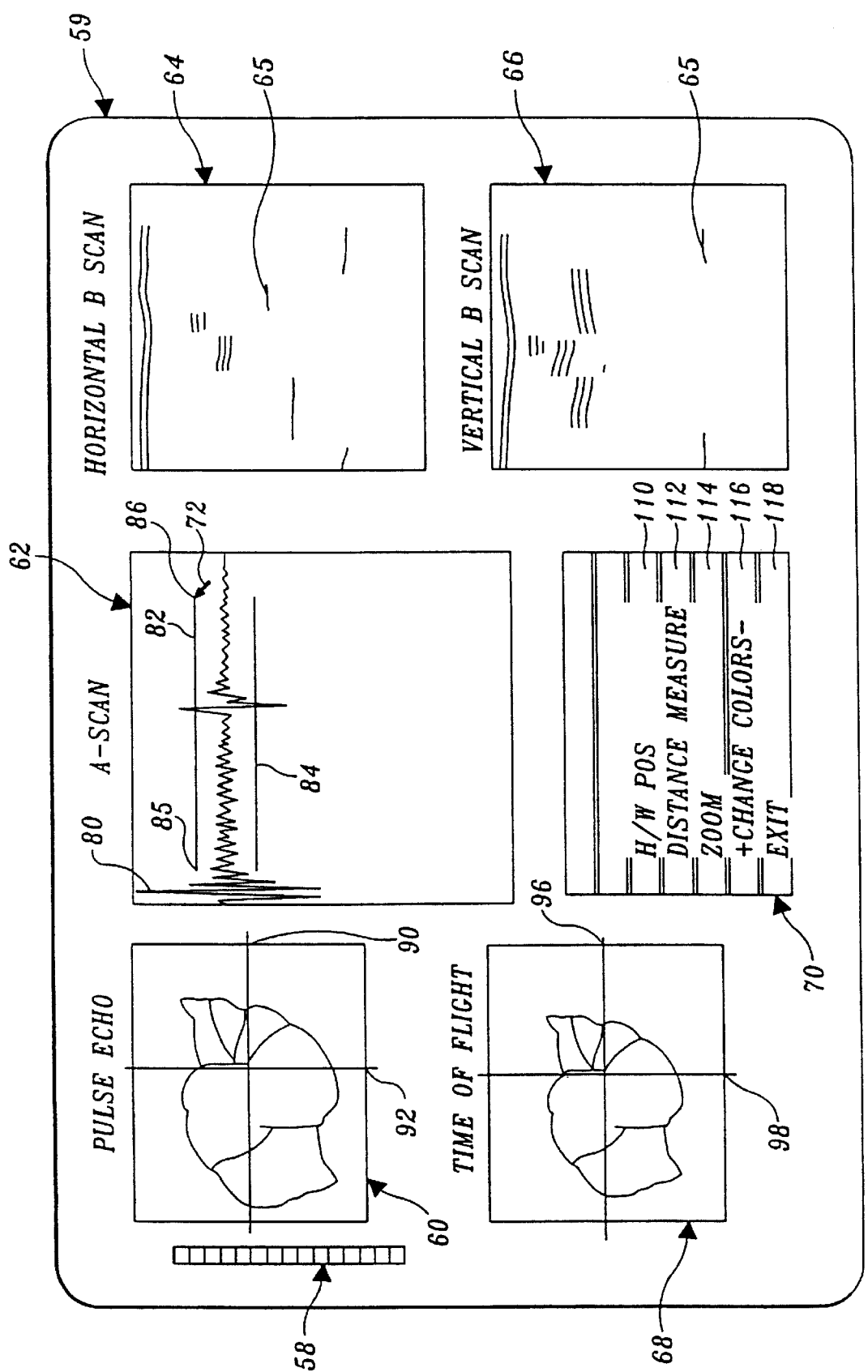
FIG. 3 illustrates one embodiment of the main screen of a graphical user interface according to present invention.
Figure 4:
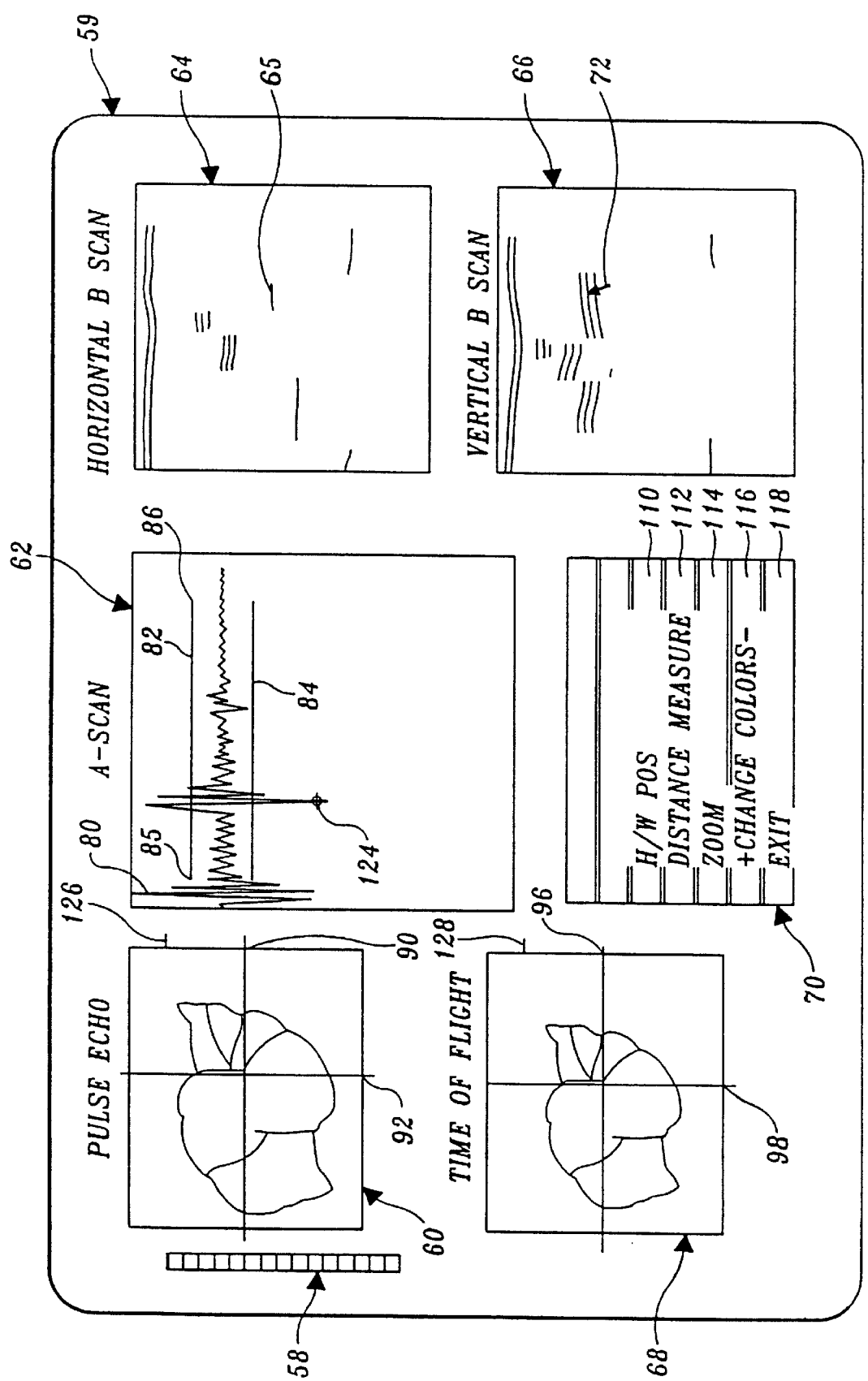
FIG. 4 illustrates how the main screen of FIG. 3 looks when a portion of the vertical B-Scan display has been selected by the user.
Figure 5:
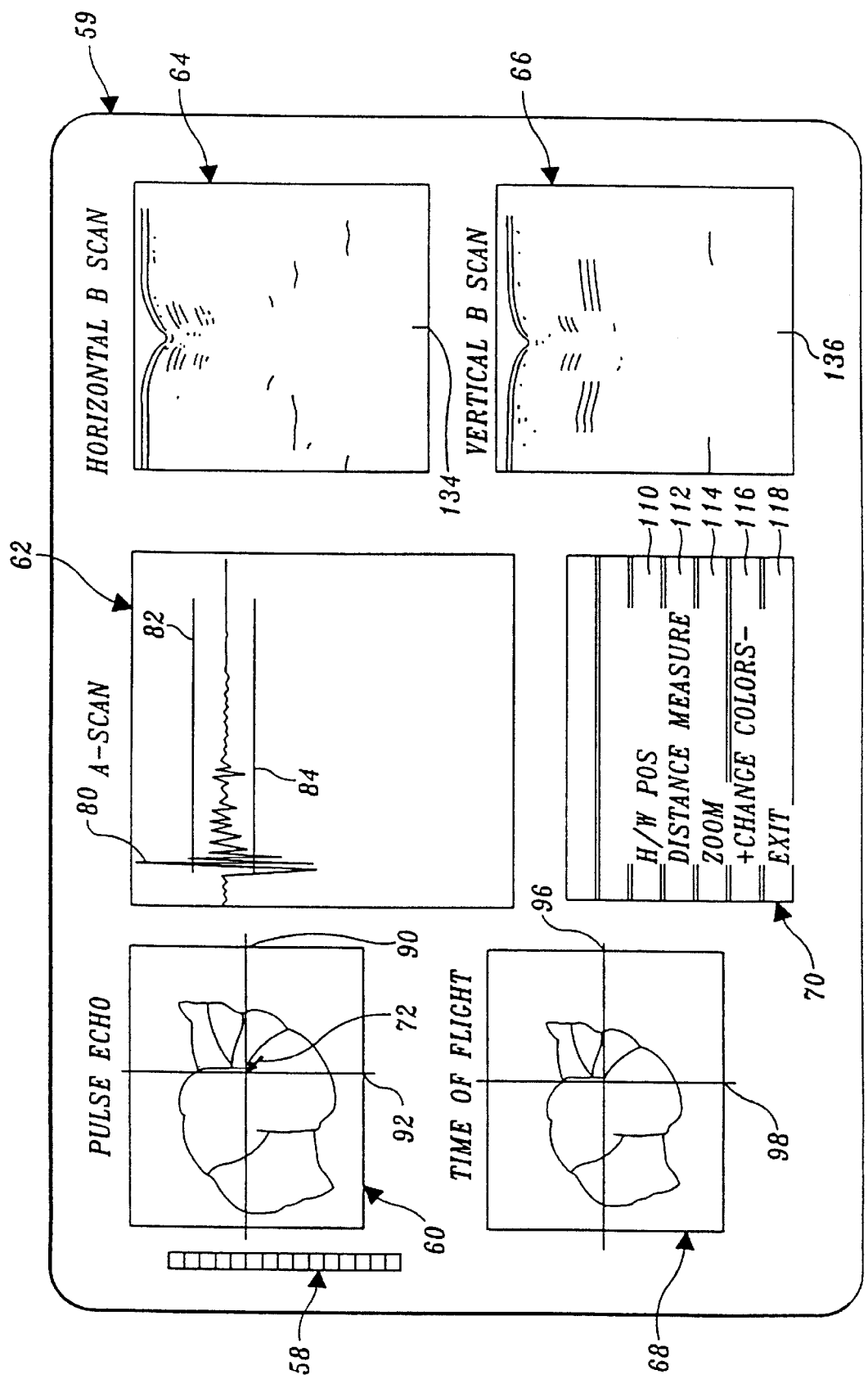
FIG. 5 illustrates how the main screen of FIG. 3 looks when a portion of the pulse echo display has been selected by the user.
Figure 6:
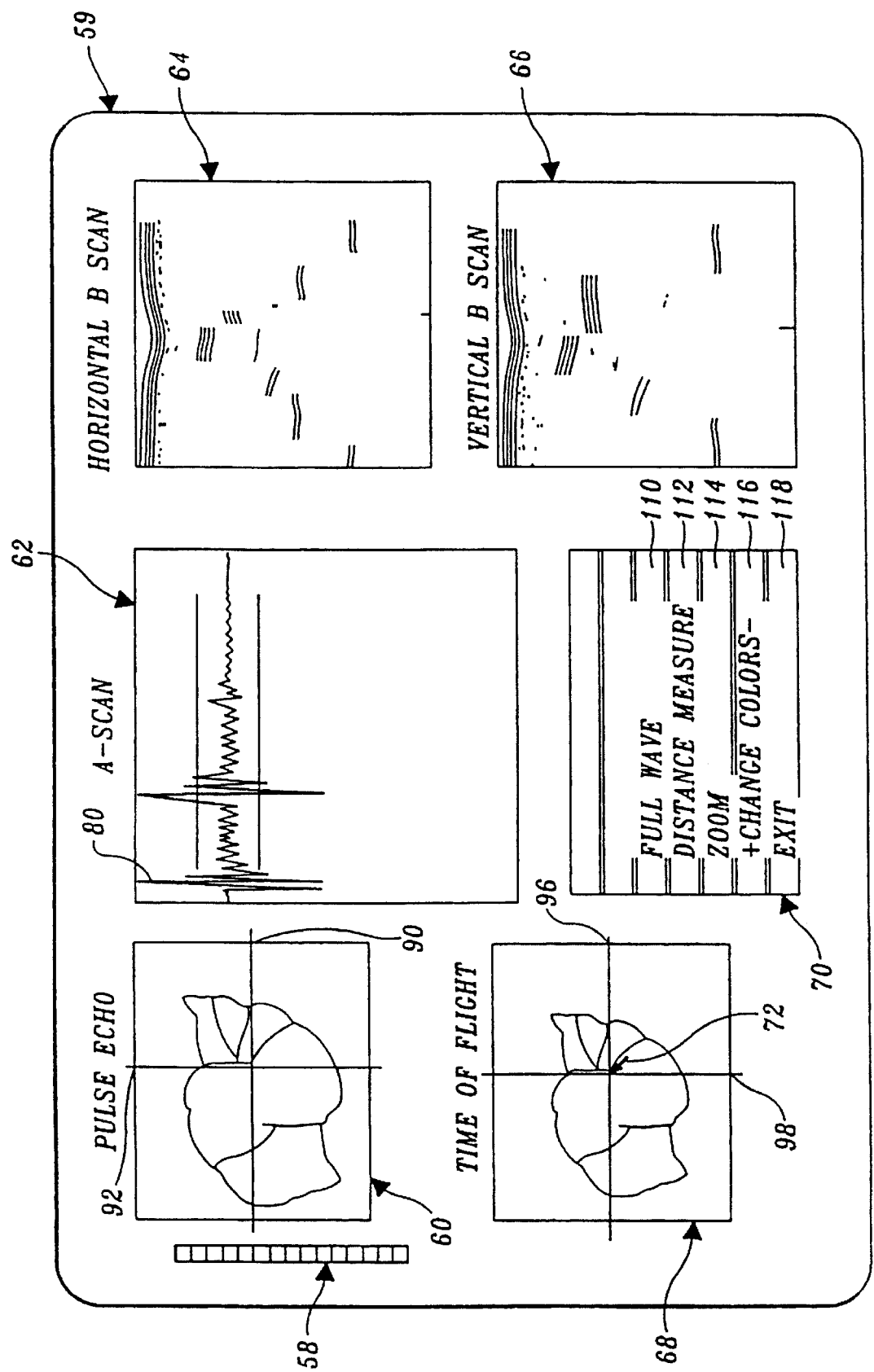
FIG. 6 illustrates how the main screen of FIG. 3 looks when a portion of the time of flight display has been selected by the user.

One preferred embodiment of a user interface output display 59 produced by the preferred embodiment of the present invention is shown in FIG. 3. The output display 59 is divided into six separate rectangular display portions. Five of the display portions contain common ultrasonic display formats, namely pulse echo 60, an A-Scan 62, a horizontal B-Scan 64, a vertical B-Scan 66, and a time of flight display 68. The sixth is a control display 70. The pulse echo 60, is located in the upper left-hand corner directly above the time of flight display 68, while the A-Scan 62 is located in the center directly above the control display 70. The horizontal B-Scan 64 is located in the upper right-hand corner directly above the vertical B-Scan 66.

The pulse echo 60 displays the ultrasonic data from the test part 32 as a top-down view through the thickness of the test part. The pulse echo 60 is divided up so that each pixel within the pulse echo graphically represents a single point on the test part at which ultrasonic data was taken. The pixels are assigned a color using a gray scale or color scale 58 such that each pixel represents the peak amplitude reflection within a single A-Scan. Each A-Scan is searched for the peak amplitude reflection within a predetermined gated portion and the value of the amplitude is recorded and used in the pulse echo 60.

As discussed above, the display 31 (FIG. 1) used in the one actual embodiment of the invention was only capable of displaying 16 colors at the resolution used. Since the A-Scan (FIG. 3) is digitized so that the amplitude ranges from 0 to 255, each gray or color scale must take into account a range of amplitudes. In this actual embodiment of the invention, the data was displayed in either the form of a half-wave positive rectification or a half-wave negative rectification, therefore, the gray or color scale represented an amplitude range from 0–128 or 128–255, and each gray or color scale represented a range of 8 in amplitude. For example, amplitudes ranging from 0 to 7 would be represented by one shade while amplitudes from 8 to 15 would be represented by a second shade of gray or color. In this embodiment of the invention, the greater the amplitude the lighter the shade of gray or color used in the pulse echo display. Obviously, other than a linear relationship can be used. Further, using monitors having greater color ranges can be used, if desired.

The time of flight display 68 is similar to the pulse echo display in that it displays the ultrasonic data as a top-down view of the test part 32. However, instead of each pixel representing the peak amplitude reflection in the gated portion of the A-Scan, each pixel represents the time it takes to receive the first reflection having an amplitude above a preset gate level. The time of flight display provides the operator with a graphical representation of the location of the discontinuity within the thickness of the test part. The operator sets the gate level or the program uses a preset gate level. Each A-Scan is then searched for the first reflection having an amplitude greater than the gate level. The time it took to receive the resulting reflection is then represented as a gray or color shade on the time of flight display. In the actual embodiment of the invention referred to above, the greater the time the darker the gray or color shade used in the time of flight display 68.

The A-Scan 62 is a graph of the digitized RF signal for a single data point 42 (FIG. 1). The operator determines which data point the A-Scan is displayed for by selecting a data point in either the pulse echo 60 or time of flight display 68 as described in more detail below.

The horizontal and vertical B-Scans 64 and 66 provide the operator with a graphical display of the A-Scans taken at data points 42 located along a cross section through the thickness of the test part 42. The horizontal B-Scan 64 displays the A-Scan data through the thickness of the test part along a cross section defined by the horizontal cross hairs 90 and 96 in the pulse echo 60 and time of flight display 68, respectively (FIG. 3). The vertical B-Scan is a graphical representation of the A-Scan data along a cross section of the test part defined by the vertical cross hairs 92 and 98 in the pulse echo 60 and time of flight display 68, respectively.

Each column of pixels in the horizontal and vertical B-Scans 64 and 66 graphically represent a single A-Scan using a gray or color scale 58. Each pixel within the horizontal and vertical B-Scans is assigned a gray shade corresponding to the amplitude of the respective data point within the A-Scan. In the actual embodiment of the invention referred to above, the top row of pixels in the horizontal B-Scan represented the amplitude of the first data point in the corresponding A-Scan. In the B-Scans, the lightest shade of gray or color represented the greatest amplitude while zero amplitude was represented by the darkest gray or color shade. In FIGS. 3–8, the color palette is inverted for ease of illustration, thus the darker portions of the data 65 in the B-Scan represent the greatest amplitudes and would appear as the lightest color on the display 31 in the actual embodiment of the invention referred to above.

The control display 70 contains a series of selection boxes that allow an operator to alter some of the display options using a cursor controlled by a keyboard 28, or a mouse 30 (FIG. 1). The selectable options include a rectification box 110 that allows the operator to select either the half-wave positive, half-wave negative, or full-wave data to be used within the pulse echo 60, time of flight display 68, horizontal B-Scan 64, and vertical B-Scan 66. The distance measure box 112 allows the operator to perform distance measurements within any of the displays and is described in more detail below. The zoom box 114 allows the operator to zoom in on portions of either the pulse echo 60 or time of flight display 68. The change colors box 116 allows the operator to select different color or gray scales 58 and the exit box 118 allows the operator to exit the program.

The present invention allows an operator to select various portions of the ultrasonic data displayed in any display and automatically revises the other displays based upon the operator's selections. Using the present invention, an operator can view the A-Scan data at individual data points, view a vertical or horizontal B-Scan at a desired location or view a pulse echo or time of flight display with any selected gate values. These options allow an operator to better understand the ultrasonic data and the nature of any flaws, voids, delaminations or other discontinuities in the test part.

Figure 9:
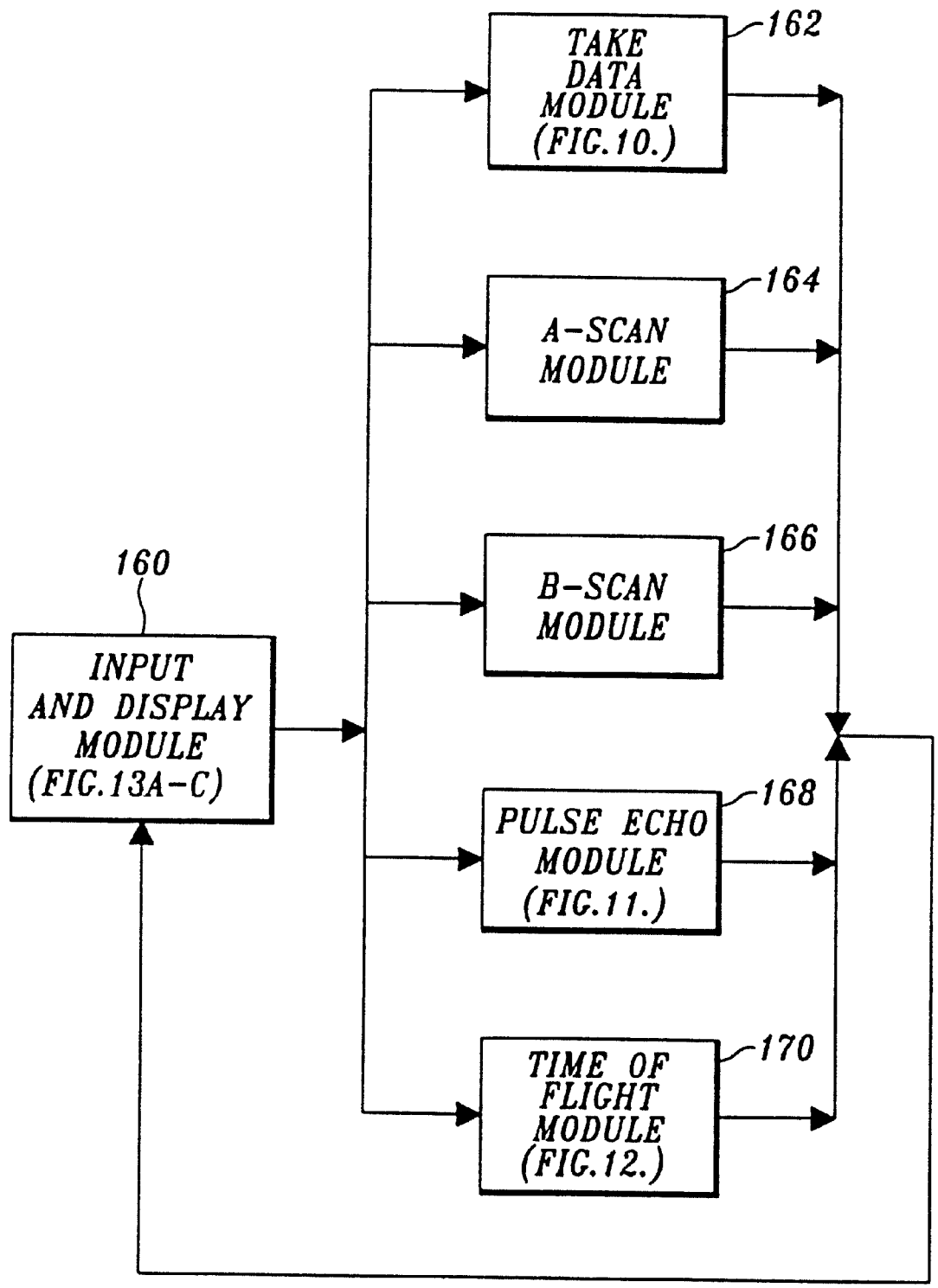
FIG. 9 is a flow chart showing the logical operation of a computer program according to the present invention.
Figure 10:
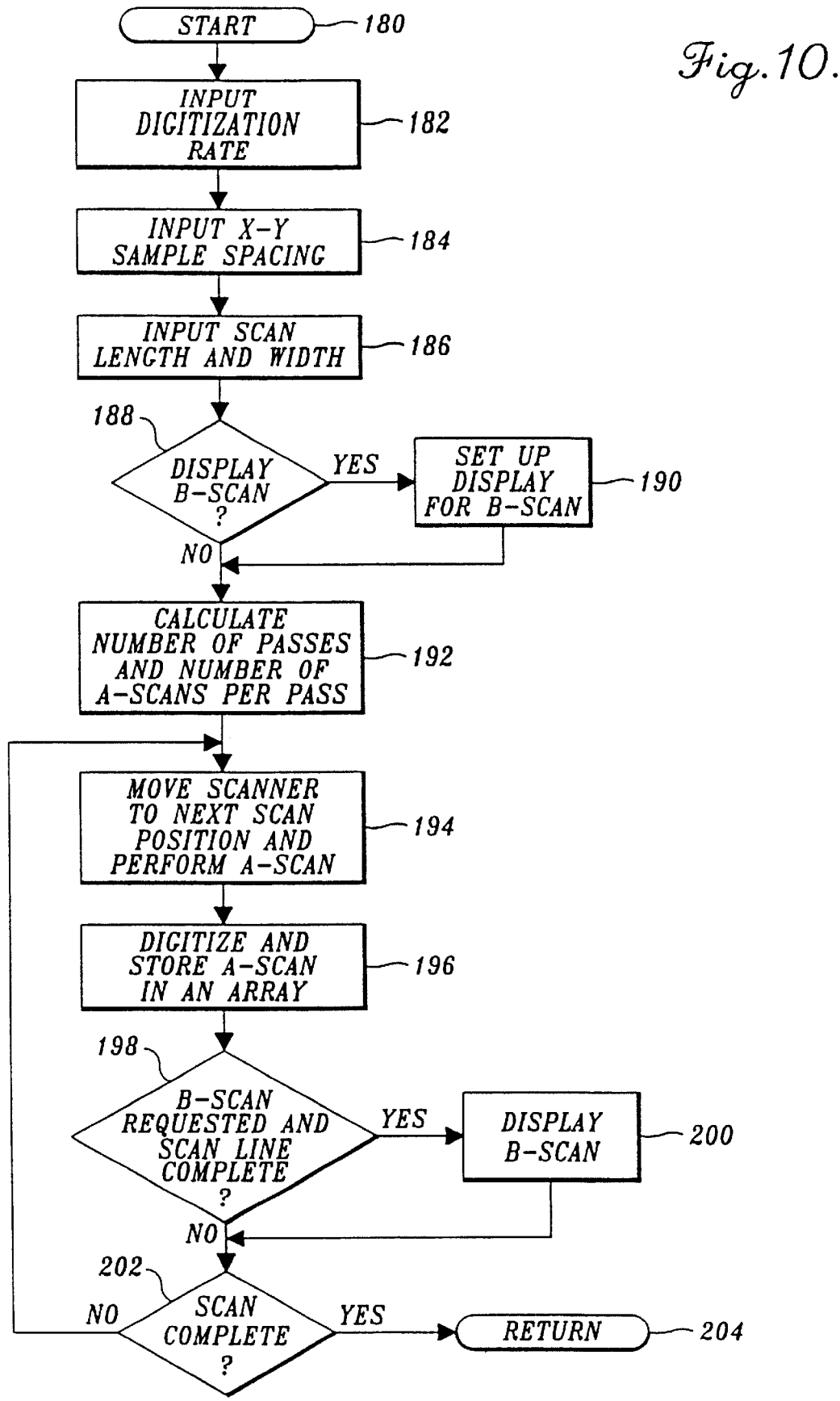
FIG. 10 is a flow chart showing the logical steps of the take data module of FIG. 9.

A flow diagram of a computer program suitable for controlling a CPU in a manner that produces the display 59 shown in FIG. 3 is illustrated in FIGS. 9–13 and described next. FIG. 9 is a flow chart that illustrates the basic organization of the computer program. The program is broken into a number of different subroutines or modules, including an input and display module 160. The input and display module 160 controls the flow of the program and receives the operator's inputs. A take data module 162 instructs the ultrasonic test apparatus 20 to take ultrasonic test data at the data points 42 on the test part 32. The ultrasonic test data is used by the input and display module 160 to supply data to and/or control other modules of the program, as well as control the display 59.

The input and display module 160 provides input to and receives output from an A-Scan module 164, a B-Scan module 166, a pulse echo module 168, and a time of flight module 170. The A-Scan module 164, B-Scan module 166, pulse echo module 168, and time of flight module 170 provide the data necessary for the input display module to display the respective data on the display 59.

The logical operation of each of the modules will now be described by reference to FIGS. 10–13. Each of the modules will first be described individually and then the interaction of the modules with the input and display module 160 will be described. The logical steps used in the take data module 162 are described with reference to the flow chart shown in FIG. 10. Upon receiving a request to take ultrasonic data from the input and display module 160, the steps of the take data module are initiated 180. If not already done, the operator is requested to input a number of data parameters, including the rate at which the RF signal is to be digitized 182, the X,Y data point spacing 184, and the length and width of the scanning pattern 186. In addition to inputting the data parameters, the operator is also asked whether or not a continuous B-Scan display is desired as the test part 42 is scanned 188. If the user responds affirmatively, the display 24 is configured, to show a B-Scan 190 at the end of each scan line as the ultrasonic transducer 22 is moved across the test part 32.

If the user does not respond affirmatively the number of passes of the ultrasonic transducer 22 and the location at which data is to be taken are calculated 192. The ultrasonic transducer 22 is instructed 194 to move to the first data point in the scanning pattern and to perform an A-Scan. As discussed above, the A-Scan may be recorded using either pulse echo ultrasonic test equipment or through transmission test equipment, as commonly known in the art, although pulse echo equipment is preferred.

As an A-Scan is performed, the entire RF waveform received by the ultrasonic transducer 22 is digitized and stored in an array location 196 in the memory of the computer 24. After the A-Scan is digitized and stored in an array within the CPU's memory, the A-Scan data is displayed at the end of each scan line as a running B-Scan if requested 198 and 200. If the user does not request that the B-Scan be displayed, the program then determines whether the entire test part has been scanned 202. If the scan is not complete, the ultrasonic transducer is moved to the position of the next data point and another A-Scan is performed. If the scan is complete, the program leaves the take data module 162 and cycles 204 to the input and display module 160.

After the test part 32 has been scanned and a complete A-Scan array produced, sufficient ultrasonic test data exists to produce the display 59 shown in FIG. 3. Further, the operator can now use the input and display module 160 to display and analyze the ultrasonic test data.

Figure 11:
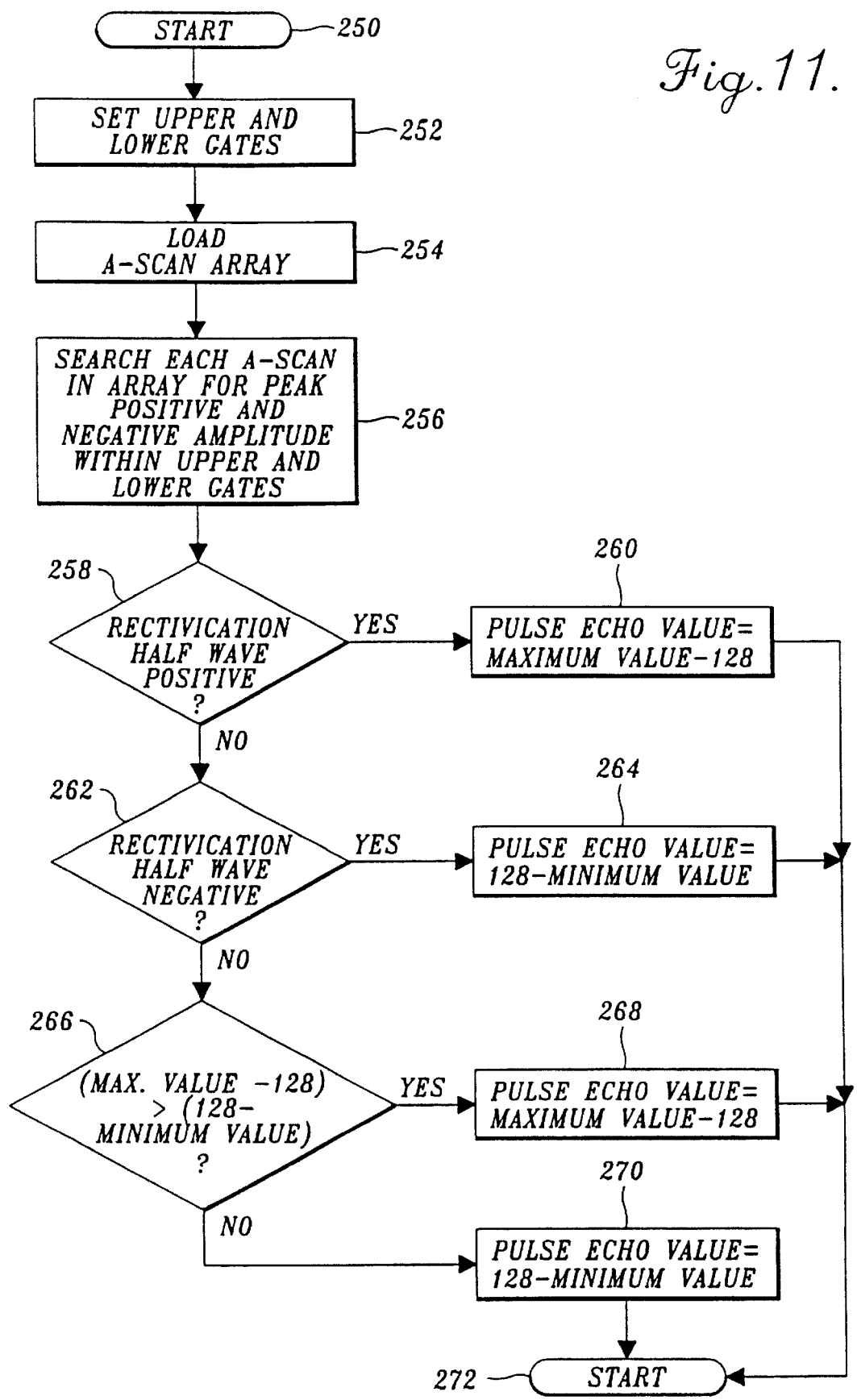
FIG. 11 is a flow chart showing the logical steps of the pulse echo module of FIG. 9.

Turning to FIG. 11, whenever the input and display module 160 requests data to display a pulse echo, the pulse echo module 168 is initiated 250. As discussed above, a pulse echo is a graphical representation of the ultrasonic data as a top-down view through the thickness of the test part. Each pixel in the pulse echo represents the amplitude of the largest reflection with a gated portion of each individual A-Scan. In order to remove the effects of large amplitude reflections caused by the front or rear surfaces of the test part on the pulse echo, it is often beneficial to set upper and lower gates 82 and 84, respectively, on the A-Scan as shown in FIG. 3. The start and stop points 85 and 86, respectively, at which the gates are set 252 (FIG. 11) are either a default value or are input by the operator as discussed below. As shown in FIG. 3, the upper and lower gates 82 and 84 are generally set to an amplitude less than or greater than the largest or smallest amplitude, respectively, of the reflection 80 caused by the front surface of the test part. The start point 85 is generally set later than the reflection 80 caused by the front surface of the test part and the stop point 86 is generally set after the reflection caused by the back surface of the test part. After the upper and lower gates 82 and 84 are set, the entire A-Scan array is loaded 254 into the pulse echo module and the gated portion of each A-Scan is searched 256 for the greatest positive amplitude and the lowest amplitude.

In the preferred embodiment, the operator selects a start point 85 by placing the cursor 72 at the desired location and depressing a selection key, the operator then places the cursor at the stop point 86 and depresses the selection key. The operator's selection of the start and stop point also determines the amplitude at which the upper and lower gates are set. The upper and lower gates are set symmetrically around the 0 volt range of the A-Scan, i.e., around an amplitude of 128 in the preferred embodiment. By selecting the desired start and stop points 85 and 86, respectively, the operator filters out portions of the ultrasonic data thus allowing irrelevant data to be ignored in order to focus on the ultrasonic data around a suspected flaw, delamination, etc.

The pulse echo module returns data 272 to the input and display module 160 in three different formats. In the first format, referred to as half-wave positive rectification, only the positive portion of the gated portion of the A-Scan is evaluated 258 and only the values of the positive peak amplitudes within the upper gate 82 minus the zero magnitude level (128 in the actual embodiment of the invention described above) are returned 260. If the rectification is not half-wave positive, the module returns to block 262. In the second format, referred to as half-wave negative rectification, only the negative portion of the A-Scan is evaluated 262 and only the values of the negative peak values of the A-Scan within the gated region are returned. The negative peak values are those equal to those having a value greater than the zero magnitude level (128) minus the minimum value. If the rectification is not half-wave negative, the module returns to block 266. Alternatively, in a third format, referred to as full-wave rectification, both the positive and the negative portions of the A-Scan within the gated region are evaluated and the greater of the rectified half-wave positive value and the half-wave negative values are returned 268, 270. If the maximum value minus 128 is greater than 128 minus the minimum value, the pulse echo value is set to the maximum value minus 128. If not, the pulse echo value is set to 128 minus the minimum value, control is then returned to the input and display module.

The A-Scan module 164 (FIG. 9) provides the input and display module 160 with the data that is displayed in the A-Scan 62 (FIG. 3). The A-Scan 62 is a graph of the digitized RF signal with time plotted along the X-axis and amplitude plotted along the Y-axis. When the input and display module 160 requests A-Scan data from a particular location on the test part, the A-Scan module 164 searches the A-Scan array created by the take data module and outputs the requested data.

The B-Scan module 166 provides the input and display module 160 with the data that is to be displayed in both the horizontal B-Scan 64 and the vertical B-Scan 66. When the input and display module 160 requests A-Scan data along the horizontal and vertical cross hairs 90 and 96 and 92 and 98 in the pulse echo and time of flight displays, respectively, the B-Scan module searches the A-Scan array produced by the take data module for the proper A-Scan and returns the data to the input and display module. The movement and position of the cross hairs is controlled in a conventional manner using either keyboard commands or a mouse.

Figure 12:
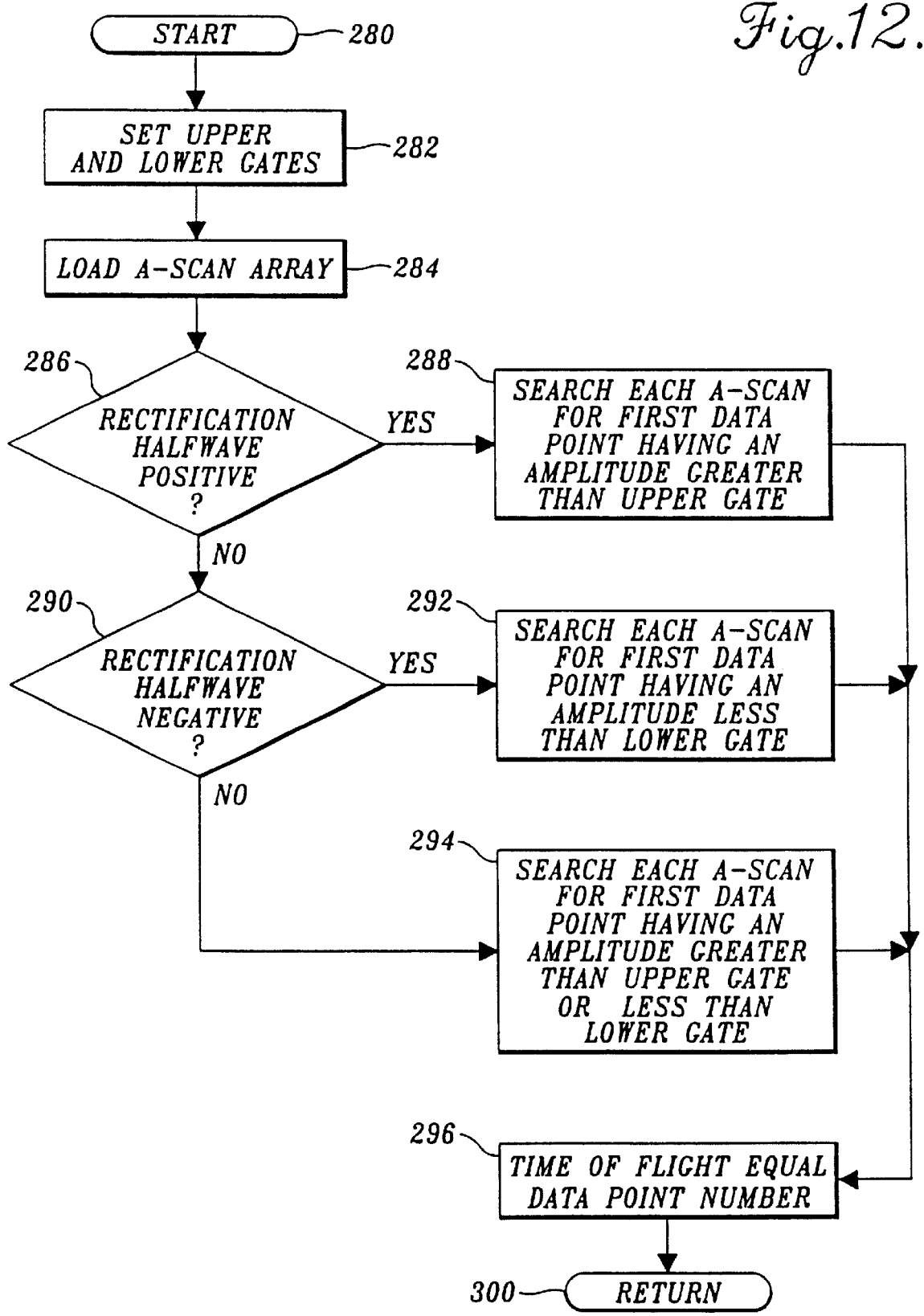
FIG. 12 is a flow chart showing the logical steps of the time of flight module of FIG. 9.

The time of flight module 170 provides the input and display module 160 with the information necessary to produce the time of flight display. As shown in FIG. 12, after being entered 280, like the pulse echo module 168, the time of flight module calls for upper and lower gates on the A-Scan data to be set 282 to prevent the large reflections from the front and back surfaces of the test part from biasing the time of flight display. The amplitude and start and stop points for the upper and lower gates may be set to default values or may be input by the operator. As discussed above, the time of flight display 68 (FIG. 3) is a graphical representation of the time it took the ultrasonic sound wave to contact a discontinuity in the test part and return to the ultrasonic transducer. Thus, the time of flight display is representative of the depth at which a test part discontinuity is located.

The data for the time of flight display 68 is obtained by searching the gated portion of the A-Scan array provided by the take data module 162 for the first data point that has an amplitude greater than or less than the upper and lower gate values, respectively, depending upon whether a half-wave positive or negative rectification is requested. The time of flight, i.e., the time it took for the ultrasonic wave to travel to and back from the discontinuity to be received by the ultrasonic transducer for the located data point is then graphically represented in the time of flight display 68 (FIG. 3) using the gray or color scale 58, as discussed above.

After setting the upper and lower gates 282, the A-Scan array is loaded 284 into the time of flight module 170. The operator is then asked 286, 290 whether the time of flight data should be calculated based upon a half-wave positive, half-wave negative, or full-wave rectification. If a half-wave positive rectification is selected 286, the gated portion of each A-Scan is searched 288 for the first data point having an amplitude greater than the upper gate value. If not, the operator is asked if a half-wave negative rectification is desired. If a half-wave negative rectification is selected 290, the gated portion of each A-Scan is searched 292 for the first data point having an amplitude less than the lower gate value. If a half-wave negative rectification is not selected 290, thereby leaving a full-wave rectification as the remaining selection, the gated portion of each A-Scan is searched 294 for the first data point having an amplitude greater than the upper gate value and for the first data point having an amplitude less than the lower gate value. The time of flights for the data points obtained during the search are then returned 296, 300 to the input and display module 160.

Figure 13A:
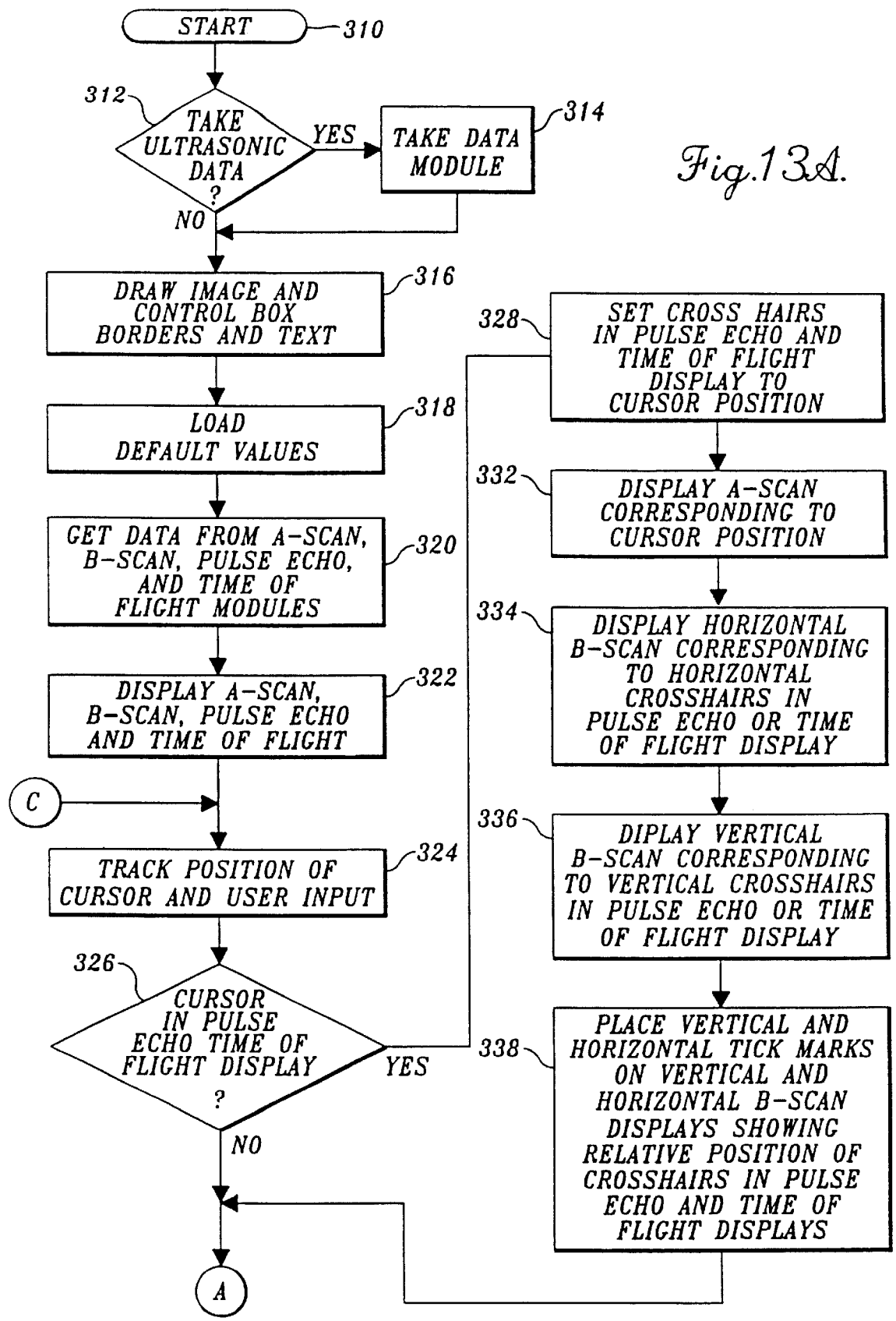
FIG. 13A–13C is a flow chart showing the logical steps of the input and display module of FIG. 9.
Figure 13B:
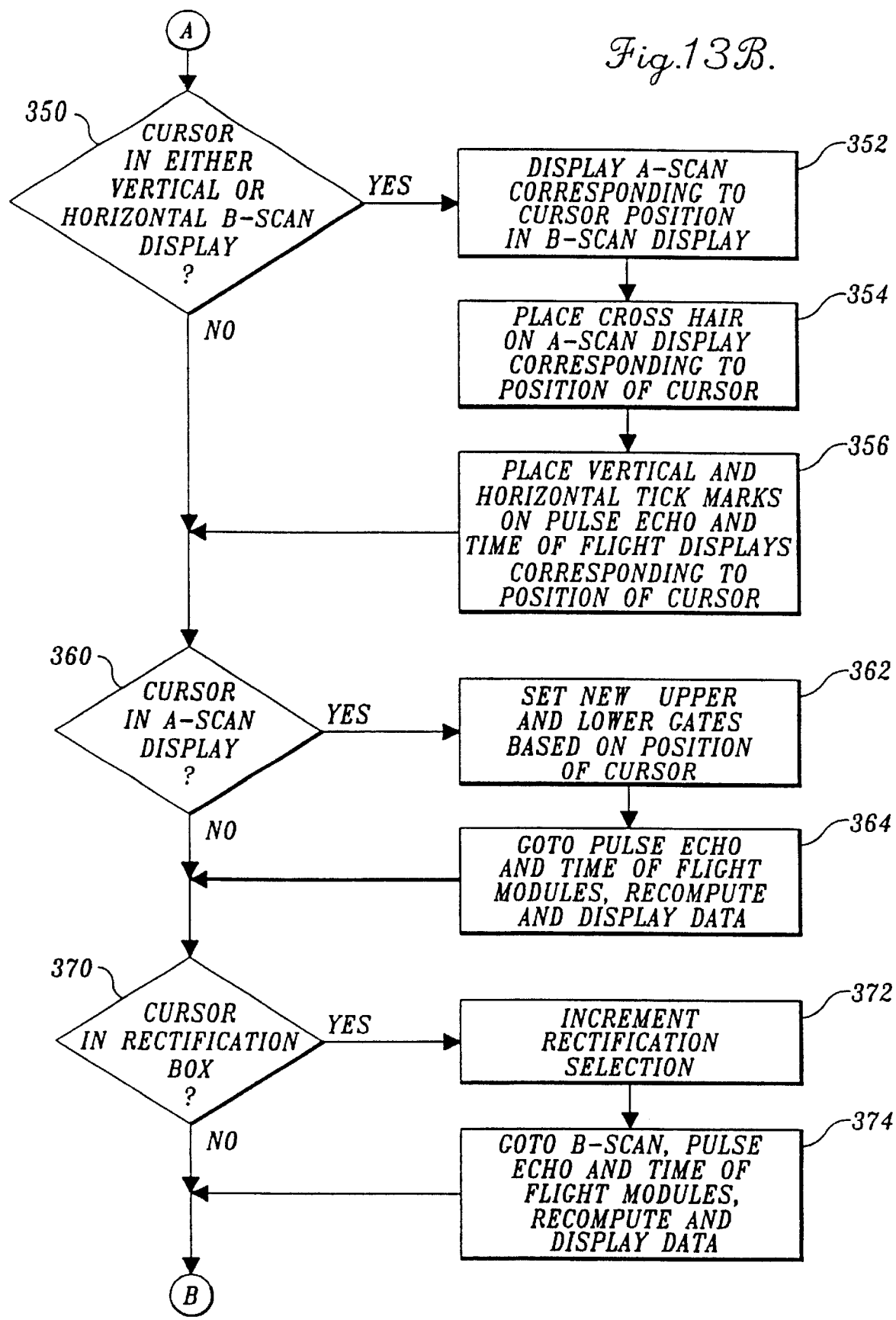
Figure 13C:
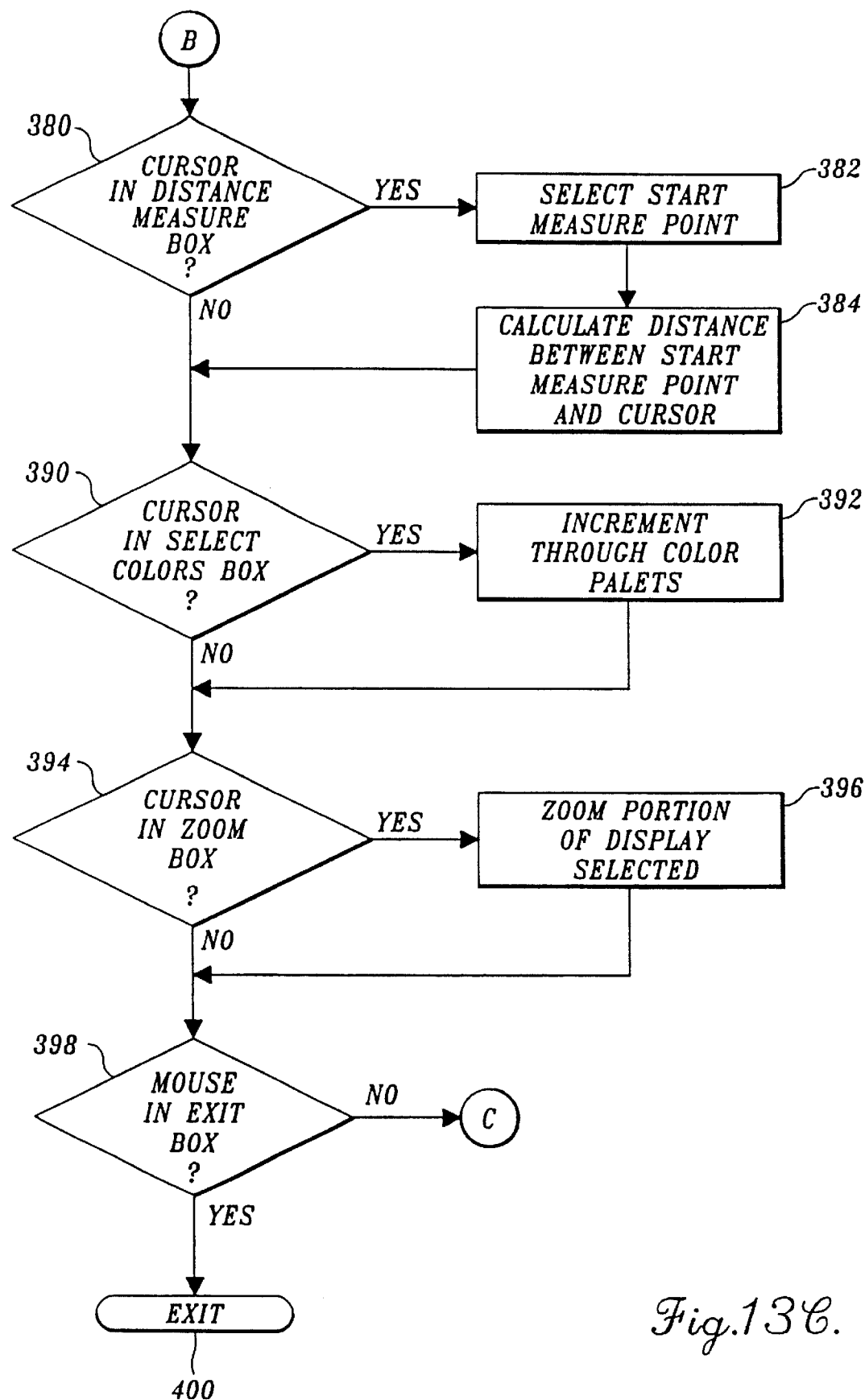

The operation of the input and display module 160 will now be described with reference to the flow chart in FIGS. 13A–C. After the module is entered 310, the operator is asked 312 whether or not ultrasonic data is to be taken. If the operator responds affirmatively, control is passed 314 to the take data module 162 (FIG. 9). After the take data module performs its function, or, if the operator answers in the negative, the borders and text for the pulse echo 60, A-Scan 62, horizontal and vertical B-Scans 64 and 66, control display 70, and time of flight display 68 are drawn 316. Default values for the display of the ultrasonic data including default amplitudes and start and stop points for the upper and lower gates 82 and 84 (FIG. 3) are then loaded from memory 318. Using the default values, the input and display module 160 requests data from the A-Scan, B-Scan, pulse echo, and time of flight modules 320. The resulting data is then plotted 322 in the corresponding portions of the display. An exemplary display produced by the input and display module is shown in FIG. 3.

Once the data for the ultrasonic test is displayed, an operator may select a number of display operations by using the keyboard 28 or the mouse 30 to position the cursor 72 (FIG. 3) over a desired portion of the displayed data. As the operator moves the cursor 72, the position of the cursor within the display 59 is tracked 324. After moving the cursor 72 to a desired location, the operator causes the display to change to the data associated with that location by depressing a key on either the mouse 30 or keyboard 28.

As the position of the cursor is tracked, tests are sequentially performed to determine the location of the cursor. First, a test 326 is performed to determine if the cursor 72 is in the pulse echo 60. If so, horizontal and vertical cross hairs 90 and 92, respectively (FIG. 6), are placed 328 at the location of the cursor. At the same time, horizontal and vertical cross hairs 96 and 98, respectively, are placed 328 on the time of flight display 68 in the same relative location as on the pulse echo display.

In addition to placing cross hairs on the pulse echo 60 and time of flight display 68 at the location of the cursor 72, the A-Scan 62 is updated 332 to correspond to the RF signal recorded for the data point selected by the cursor. As the horizontal and vertical cross hairs 90 and 92 are placed on the pulse echo, the horizontal and vertical B-Scans 64 and 66 are also redrawn 334, 336 so that they display the ultrasonic data for the data points located along the horizontal and vertical cross hairs 90 and 92, respectively. Thus, the horizontal B-Scan 64 displays the occurrence of discontinuities along the horizontal cross hair 90 while the vertical B-Scan 66 displays the occurrence of discontinuities along the vertical cross hair 92. A tick mark 134 (FIG. 5) is also placed 338 along the bottom of the border of the horizontal B-Scan, and a tick mark 136 is placed 338 along the bottom of the border for the vertical B-Scan. The tick marks 134 and 136 show the position across the horizontal and vertical B-Scans 64 and 66 of the data point selected by the cursor 72 in the pulse echo.

Next, a test 350 is made to determine if the cursor 72 is located in either the horizontal or vertical B-Scan displays 64 and 66. If so, the A-Scan 62 is updated 352 to display the RF signal recorded for the data point selected by the cursor 72. A symbol 124, such as a cross hair, is also placed 354 on the A-Scan 62 (FIG. 4) at the data point in the A-Scan that corresponds to the data point in the B-Scan selected by the cursor 72. The symbol 124 allows the operator to immediately identify the data in the A-Scan that corresponds to the data point selected by the cursor 72.

Horizontal tick marks 126 and 128 are placed 356 along the vertical borders of the pulse echo 60 and time of flight display 68, respectively. The horizontal tick marks 126 and 128 mark the location of the data point selected by the cursor 72 along the vertical cross hairs 92 and 98, respectively. Similarly, if the operator selected a data point within the horizontal B-Scan 64, tick marks would be placed along the horizontal borders on the pulse echo and time of flight displays to indicate the location of the selected data point along the horizontal cross hairs 90 and 96, respectively.

Next, a test 360 is made to determine if the cursor is located on a portion of the A-Scan. If so, the amplitude and start and stop points 85 and 86 for the upper and lower gates 82 and 84 (FIG. 3) used to filter the ultrasonic data are reset 362. The values are determined by the operator first selecting a new start point 86 and then selecting a new stop point 86, thus selecting the amplitude and start and stop points for the upper gate 82. The lower gate 84 is then step symmetrically around the zero volt value, i.e., 128 in the preferred embodiment, using the same start and stop points 85 and 86, respectively. After the upper and lower gates are set, a pass 364 is made through the pulse echo and time of flight modules, during which the ultrasonic test data to be displayed is recomputed in the manner previously described, and the related displays are updated after which control is returned to block 370.

The operator may also select a number of different display options from the control display 70. Thus, the next test 370 is to determine if the cursor 72 is within the rectification box 110. If so, the rectification options of half-wave positive, half-wave negative, and full-wave rectification are incremented 372, as determined by the operator. In order to prevent the operator from waiting all of the displays to be updated, the B-Scan, pulse echo and time of flight displays are updated upon selecting an individual display 374 after which control is returned to block 380. Alternatively, after the operator's selection, a pass could be made through the pulse echo 168, B-Scan 166, and time of flight modules 170 to recompute and update the related displays.

Figure 7:
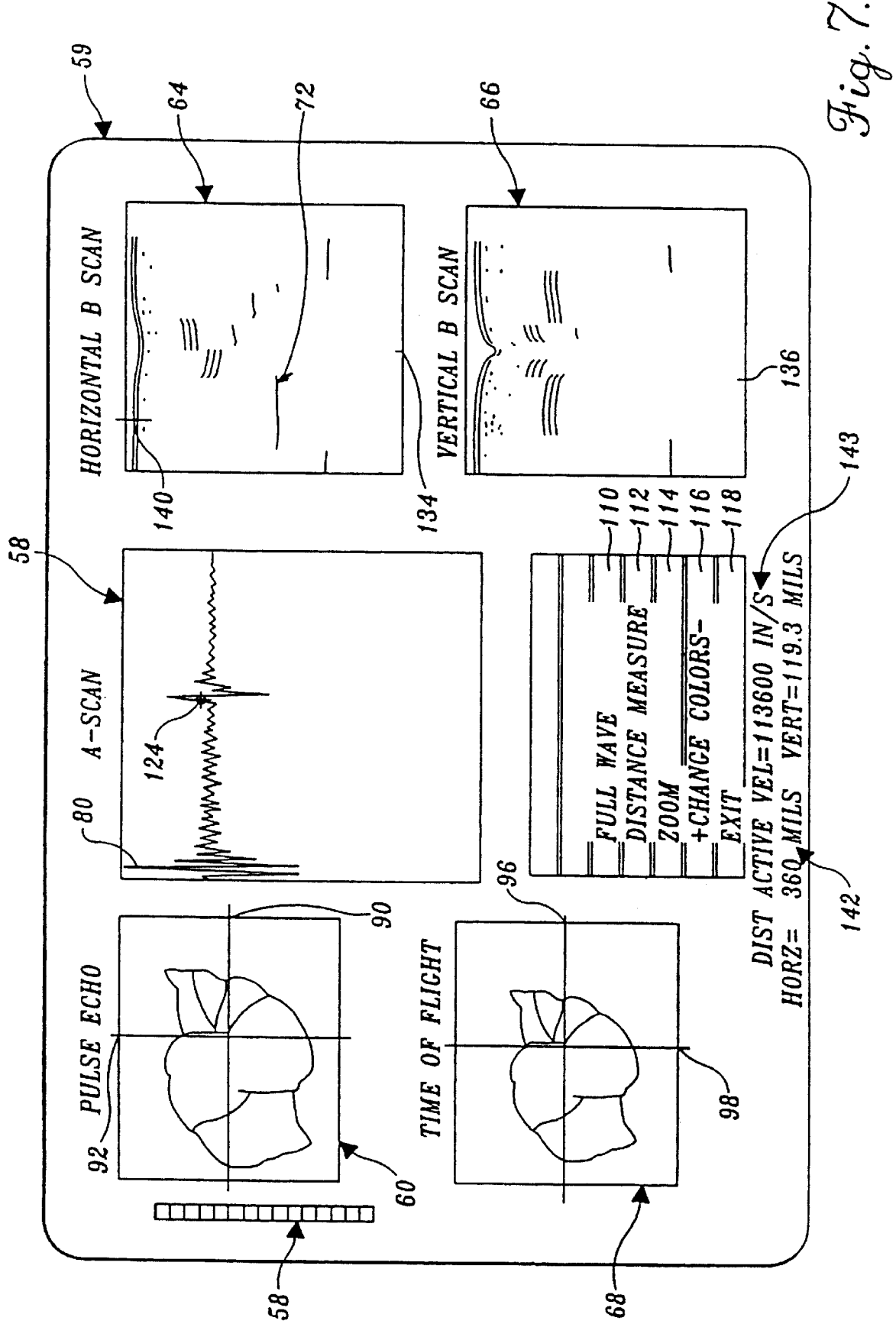
FIG. 7 illustrates how the main screen of FIG. 3 looks when the user has selected the distance measure option in the horizontal B-Scan display.

Next, a test 380 is made to determine if the cursor is in the distance measure box 112 (FIG. 7). If so, a start measure point is selected 382 by repositioning the cursor 72 to the desired location within either the horizontal B-Scan 64, vertical B-Scan 66, pulse echo 92, or time of flight display 68. In the example shown in FIG. 7, the start measure point has been selected and is marked by a cross hair 140 in the horizontal B-Scan 64. After selecting the start point, both the distances along the X and Y axis of the display between the start measure point and the cursor 72 are calculated 384 and displayed 142 as shown in FIG. 7. The speed of sound 143 used to calculate the distances measured within the displays is also displayed so that the operator may determine whether or not the proper speed of sound for the particular test part tested is being used.

Next, a test 390 is made to determine if the cursor is in change color box 116. If so, the program increments 392 through various color palettes. When a new color palette is selected by the operator pressing a key of the keyboard 28 or clicking the mouse 30, the colors used within the various displays are updated.

Figure 8:
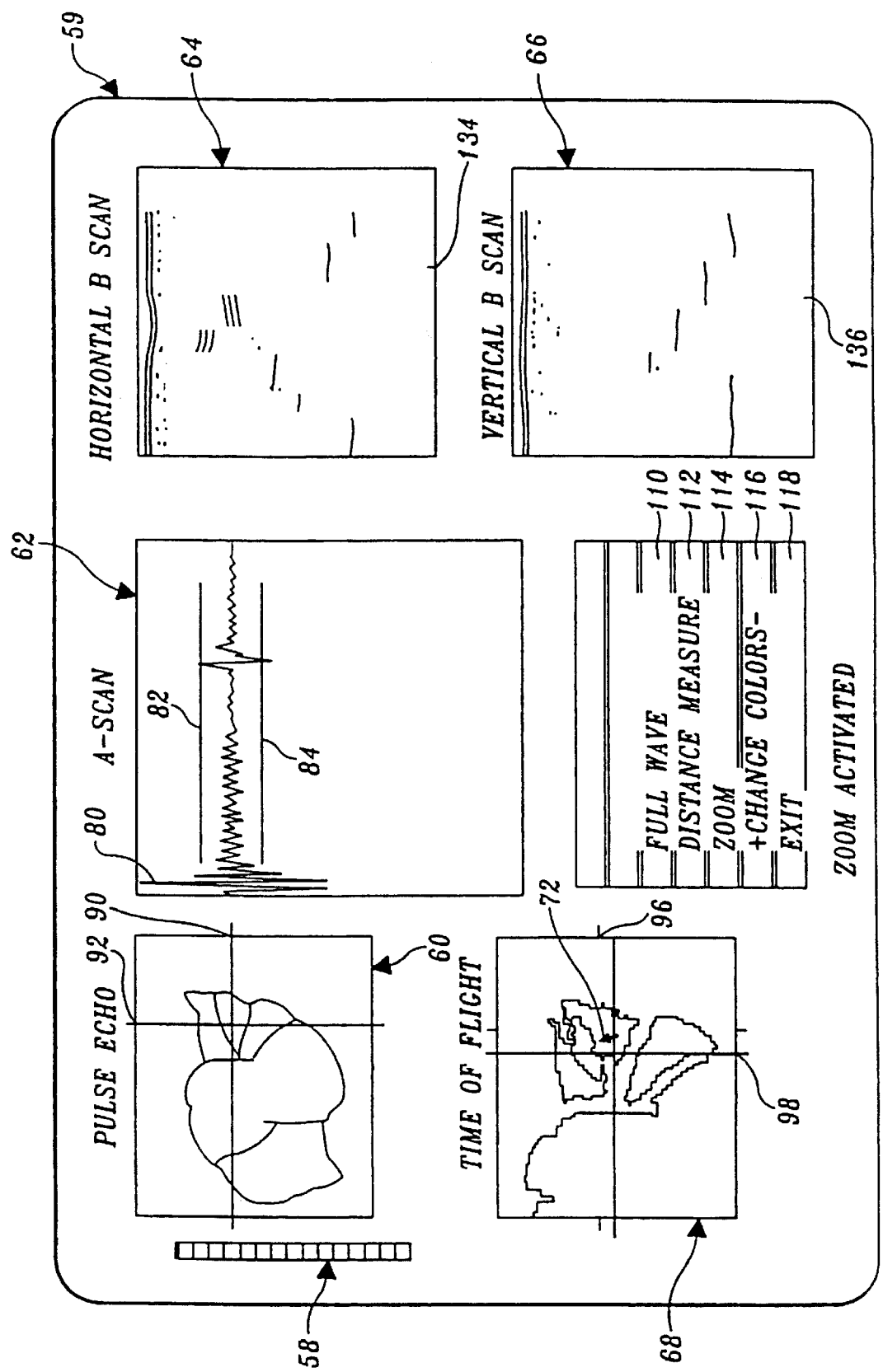
FIG. 8 illustrates how the main screen of FIG. 3 looks when the user has selected the zoom option in the time of flight display.

Next, a test 394 is made to determine if the cursor is in the zoom box 114 as shown in FIG. 8. If so, the portion of either the pulse echo or time of flight display selected is zoomed 396 in order to provide a better view of the data related to the position when the cross hair is located on the related display. The program continues to cycle through the foregoing tests until the cursor is placed in the exit box 398 and the mouse clicked or a suitable key depressed at which time the program exists 400.

Figure 14:
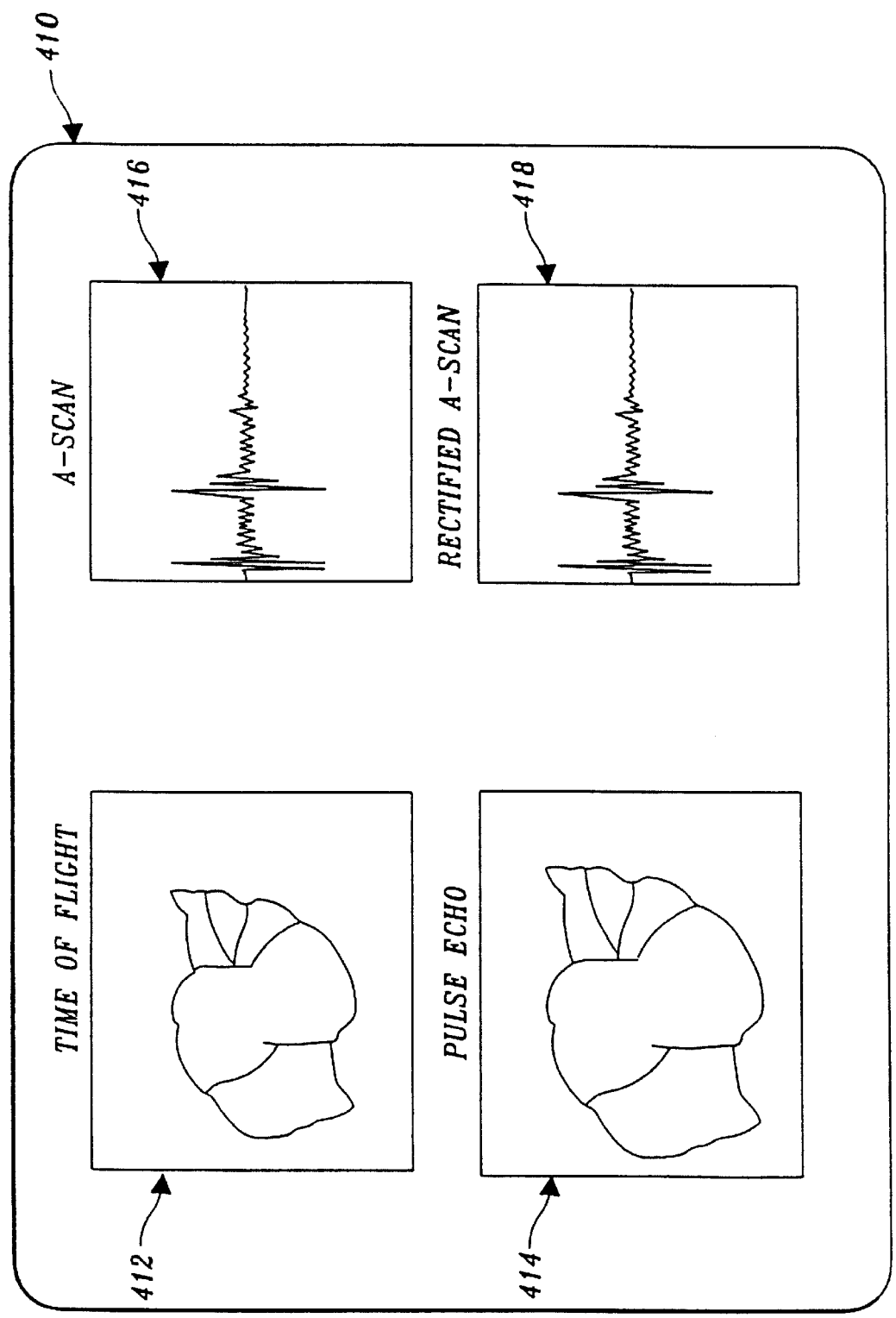
FIG. 14 illustrates another embodiment of the main screen of a graphical user interface according to present invention.

A second display configuration 410, according to the present invention, is shown in FIG. 14. In the second display configuration, a pulse echo 414 is located in the bottom left corner of the display directly below a time of flight display 412. On the right side of the display, an A-Scan 416 is located directly above a full-wave rectified A-Scan 418. In still other embodiments, the time of flight or the other data display formats could be replaced by horizontal or vertical B-Scans.

While a preferred embodiment of the invention has been illustrated and described, it will be appreciated that various changes can be made therein without departing from the spirit and scope of the invention. For example, the various data display formats could be reoriented or resized. Hence, within the scope of the appended claims it is to be understood that the invention can be practiced otherwise than as specifically described herein.

The embodiments of the invention in which an exclusive property or privilege is claimed are defined as follows:

1. A system for analyzing and displaying ultrasonic test data produced by an ultrasonic test apparatus for a test part, the system comprising:
   (a) a display for simultaneously displaying ultrasonic test data in at least two display portions, including a first display portion and a second display portion, each of said display portions displaying ultrasonic test data in a format selected from the group consisting of an A-Scan, a B-Scan, a pulse echo, and a time of flight format, said display presenting ultrasonic test data in a manner such that locations on said display correspond to locations on said test part;
   (b) an input device responsive to an operator's input for selecting at least one location on said first display portion, wherein said at least one location corresponds to a selection of the ultrasonic test data as displayed within said first display portion, and producing display location data, wherein said display location data can be produced a plurality of times in response to a plurality of input selections by the operator; and
   (c) control means coupled to said display and said input device for receiving the display location data from said input device, determining ultrasonic test data parameters corresponding to the display location data, filtering out portions of the ultrasonic test data based on the combination of the ultrasonic test data parameters and the format of said second display portion, and for causing said second display portion to update said display of ultrasonic data by displaying portions of the ultrasonic test data that have not been filtered out, wherein said filtering and updating of data can be done a plurality of times in response to a plurality of display location data produced by said input device.

2. The system of claim 1, wherein the display simultaneously displays the ultrasonic test data in at least three display portions, including a third display portion displaying test data in a format selected from the group consisting of A-Scan, B-Scan, pulse echo and time of flight, and wherein said control means additionally filters out portions of the ultrasonic test data based on the combination of the ultrasonic test data parameters and the format of said third display portion, causing said third display portion to update said display of ultrasonic data by displaying portions of the ultrasonic test data that have not been filtered out by the filtering corresponding to said third display portion.

3. The system of claim 1, wherein the input device allows the operator to select two locations on one of the display portions, and wherein the control means includes a processor that calculates the distance between the locations on the test part related to the two selected locations on one of the display portions.

4. The system of claim 1, wherein said first display portion displays data in any display format other than an A-Scan format, and wherein said ultrasonic test data parameters include the specification of at least one location on the test part, and wherein said second display portion displays data related to said at least one location in an A-Scan format.

5. The system of claim 1, wherein said first display portion displays test data in an A-Scan format, and said control means filters out ultrasonic test data outside of a specified depth within the test part, said depth being determine by a selection of a location within said first display portion.

6. The system of claim 1, wherein said first display portion displays test data in in A-Scan format, said ultrasonic test data parameters include the specification of an amplitude of ultrasonic energy, and the control means causes the second display portion to filter out ultrasonic test data outside of said amplitude of ultrasonic energy.

7. The system of claim 1, wherein:
   (a) said input device is responsive to an operator's input for selecting at least one location on said second display portion, and producing second display location data; and
   (b) said control means determines second ultrasonic test data parameters corresponding to said second display location data, filters out portions of the ultrasonic test data based on the combination of said second ultrasonic test data parameters and the format of said first display portion, and causes said display to update sad first display portion by displaying portions of the ultrasonic test data that have not been filtered out.

8. The system of claim 1, wherein said ultrasonic test data parameters include the specification of at least one location on the test part, and wherein the display simultaneously displays the ultrasonic test data in a first B-Scan format using the ultrasonic data taken along a first axis of the test part passing through the specified location on the test part and in a second B-Scan format using the ultrasonic test data taken along a second as of the test part that also passes through the specified location on the test part, said simultaneous display thereby presenting to the operator a view along three different dimensions of ultrasonic test data taken from the area surrounding the location on the test part.

9. The system of claim 8, wherein the display simultaneously displays the ultrasonic test data in at least three display portions, and wherein said first display portion displays test data in a format other than B-Scan, thereby presenting to the operator a view along three different dimensions of ultrasonic test data taken from the area surrounding the location on the test part, said view being manipulated in a unitary manner by reference to said first display portion.

10. The system of claim 1, wherein said first display portion displays ultrasonic test data in a pulse echo format and said control means causes a horizontal and a vertical cross hair to be produced on said first display portion at the selected location.

11. The system of claim 10, wherein said second display portion displays the ultrasonic test data in a horizontal B-Scan format, and said display also displays data in a third display portion, said third display portion displaying the ultrasonic test data in a vertical B-Scan format, wherein said control means determines a horizontal line on the test part corresponding to the horizontal cross hair and causes said second display to display ultrasonic test data taken along the horizontal line, and wherein said control means determines a vertical line on the test part corresponding to the vertical cross hair and causes said third display to display ultrasonic test data taken along the vertical line, the simultaneous display of said horizontal B-Scan format and said vertical B-Scan format thereby presenting to the operator a view along three different dimensions of ultrasonic test data taken from the area surrounding a point in a test part, said view being manipulated in a unitary manner by reference to said first display portion.

12. The system of claim 1, wherein said first display portion displays data in a first format selected from the group consisting of pulse echo and time of flight, the input device allows the operator to select a portion of said first display portion, and the control means causes the display to display an enlarged view of the selected portion of said first display portion.

13. The system of claim 12, wherein said second display portion displays data in a second format selected from the group consisting of pulse echo and time of flight, wherein said second format is different from said first format, and the control means causes the display to display an enlarged view of the portion of said second display portion corresponding to the selected portion of said first display portion, thereby allowing the combination of said first display portion and said second display portion to display test data corresponding to an identical section of the test part.

14. The system of claim 1, wherein said ultrasonic test data parameters include the specification of at least one location on the test part.

15. The system of claim 14, wherein said first display portion displays test data in an A-Scan format, said at least one location on the test part indicates a depth on the test part, and the control means filters out ultrasonic test data based on said depth for display on said second display portion.

16. The system of claim 15, wherein said ultrasonic test data parameters include the specification of a beginning and an ending depth on the test part, and the control means filters out ultrasonic test data outside of the beginning and ending depths for display on said second display portion.

17. In a computer system including a display, an input device responsive to an operator's input, a processor for controlling the display, memory means for storing ultrasonic test data obtained from a test part and programs for controlling the processor, the improvement comprising a user interface program for analyzing and displaying said ultrasonic test data obtained from a test part, said user interface program controlling said processor such that:

(a) said display simultaneously displays the ultrasonic test data in at least two formats selected from the group consisting of an A-Scan, a pulse echo, a B-Scan, and a time of flight format;

(b) after said display has displayed the ultrasonic test data in at least one format, said processor responds to an operator using said input device to select at least one location on said display, wherein said at least one location corresponds to the ultrasonic test data displayed in one of said at least two formats;

(c) said processor determines the ultrasonic test data corresponding to the selected location on the display, and further determines the locations on the test part corresponding to the location on the display;

d) said processor filters out a portion of the ultrasonic test data, said filtering being determined by said locations on the test part and a second one of at least two formats;

e) said processor instructs said display to update said second format in response to the operator's selection using a portion of the ultrasonic test data that has not been filtered out, and is related to said selected location; and f) said display updates said second other format in response to said processor's instructions.

18. The improvement claimed in claim 17, wherein the display simultaneously displays the ultrasonic test data in at least three formats, including an A-Scan, a pulse echo, and a B-Scan format, wherein the operator's selection can be made on any one of said three formats, and wherein said processor updates the other two of said formats in response to the operator's selection, thereby providing three different views of the ultrasonic test data related to a location on the test part, said views being manipulable by reference to any one view.

19. The improvement claimed in claim 17, wherein the display simultaneously displays the ultrasonic test data in an A-Scan, a pulse echo and a time of flight format.

20. The improvement claimed in claim 17, wherein the display simultaneously displays the ultrasonic test data in A-Scan, B-Scan, pulse echo, and a time of flight formats, each in a different portion of the display.

21. The improvement claimed in claim 17, wherein the processor responds to the operator using the input device to select a portion of one of the display formats by updating the A-Scan using the ultrasonic test data related to the operator's selection.

22. The improvement claimed in claim 17, wherein one of said formats comprises a pulse echo, and the processor responds to the operator using the input device to select a location in the pulse echo format by causing a horizontal and a vertical cross hair to be placed on the pulse echo format at the selected location.

23. The improvement claimed in claim 17, wherein the processor causes the display to produce a vertical B-Scan format using the ultrasonic test data related to the location of the vertical cross hair and a horizontal B-Scan format using the ultrasonic test data related to the location of the horizontal cross hair, the simultaneous display of said vertical B-Scan format and said horizontal B-Scan format, thereby presenting to the operator a view along three different dimensions of ultrasonic test data taken from the area surrounding a point in a test part, said view being manipulated in a unitary manner by reference to said vertical B-Scan format and said horizontal B-Scan format.

24. The improvement claimed in claim 17, wherein the processor responds to the operator using the input device to select a location in one of the formats by causing the display to display the ultrasonic test data related to the selected location as an A-Scan.

25. The improvement claimed in claim 17, wherein the processor responds to the operator using the input device to select two locations in one of the formats by calculating the distance between the locations on the test part related to the two locations selected by the operator and by causing the display to display said distance.

26. The system of claim 17, wherein said processor responds to the operator using said input device to select two locations in one of said at least two formats by determining the locations on the test part related to said two locations selected by the operator and by causing said display to update said other format by filtering out test data that does not correspond to locations on the test part between the two locations on the test part.

27. The improvement claimed in claim 17, wherein said display displays the ultrasonic test data in an A-Scan format, said processor responds to an operator using said input device to select at least one location on said A-Scan format, wherein said location corresponds to an amplitude of ultrasonic energy, and said processor filters out ultrasonic test data outside of said amplitude of ultrasonic energy, said processor causing a second display portion to display said filtered ultrasonic test data.

28. The improvement claimed in claim 17, wherein said display simultaneously displays the ultrasonic test data in pulse echo and time of flight formats, each in a different portion of the display, the input device allows the operator to select a portion of either of said formats, and the processor causes the display to display an enlarged view of the selected portion in both of said display formats.

29. The system of claim 17, wherein the processor responds to the operator using the input device to select two locations in one of the formats by determine the locations on the test part related to the two locations selected by the operator and by causing said display to update said other format by filtering out test data related to test part locations that do not fill within the two selected locations on the test part.

30. The improvement claimed in claim 17, wherein the display simultaneously displays the ultrasonic test data in a first B-Scan format along one axis of the test part in one portion of the display and displays the ultrasonic test data in a second B-Scan format along a second axis of the test part in a second portion of the display, wherein said processor responds to the operator using said input device to select a location on either one of said B-Scan formats, thereby presenting to the operator a view along three different dimensions of ultrasonic test data taken from the area surrounding a point in a test part.

31. The improvement claimed in claim 30, wherein the display simultaneously displays the ultrasonic test data in a A-Scan, a pulse echo and a time of flight format.

32. A method of analyzing and displaying ultrasonic test data obtained from a test part comprising the steps of:
  (a) storing the ultrasonic test data in a storage device;
  (b) simultaneously displaying the ultrasonic test data in at least two formats selected from the group consisting of an A-Scan, a pulse echo, a B-Scan, and a time of flight format;
  (c) determining a portion of the displayed ultrasonic test data indicative of a characteristic of the test part;
  d) selecting a location on one of said at least two formats, said location corresponding to the portion of the displayed ultrasonic test data indicative of a characteristic of the test part;
  e) determining the ultrasonic test data related to the selected location;
  f) filtering out portions of the ultrasonic test data based on a combination of said determined ultrasonic test data and the other of said at least two formats; and
  g) updating the other of said at least two formats using the ultrasonic data that have not been filtered out.

33. The method of claim 32, wherein the displaying step comprises displaying the ultrasonic test data in an A-Scan format and at least two formats selected from the group consisting of pulse echo, B-Scan, and a time of flight.

34. The method of claim 32, wherein the displaying step comprises displaying the ultrasonic test data in a first B-Scan format along a first axis of the test part passing through the selected location and in a second B-Scan format along a second axis of the test part passing through the selected location.

35. The method of claim 32, wherein the displaying step comprises displaying the ultrasonic test data in pulse echo format and the selecting step comprises selecting a location in the pulse echo, and wherein the method further comprises the steps of displaying a horizontal cross hair and a vertical cross hair on the pulse echo at the selected location and displaying a vertical B-Scan based on ultrasonic test data along the vertical cross hair and a horizontal B-Scan based on ultrasonic test data along the horizontal cross hair.

36. The program of claim 32, wherein the selecting step further comprises selecting two locations on one of the formats and the method includes the further steps of determining the distance between the locations on the test part related to the two selected locations.

37. The method of claim 32, wherein the displaying step further comprises displaying the ultrasonic test data in at least one of a pulse echo and a time of flight format and the selection step further comprises selecting a portion of said pulse echo or time of flight format and the method includes the further steps of displaying an enlarged view of the selected portion of the selected format.

38. A system for analyzing and displaying ultrasonic test data produced by an ultrasonic test apparatus for a test part, the system comprising:
  (a) a display for displaying ultrasonic test data in a format selected from the group consisting of an A-Scan, a B-Scan, a pulse echo, and a time of flight format;
  (b) an input device responsive to an operator's input for selecting two locations on said display, and
  (c) control means coupled to said display and said input device, wherein said control means calculates the distance between the locations on the test part related to the two selected locations on said display.

39. In a computer system including a display, an input device responsive to an operator's input, a processor for controlling the display, memory means for storing ultrasonic test data obtained from a test part, and programs for controlling the processor, the improvement comprising a user interface program for analyzing and displaying said ultrasonic test data obtained from a test part, said use interface program controlling said processor such that:
  (a) said display displays the ultrasonic test data in a format selected from the group consisting of an A-Scan, a pulse echo, a B-Scan, and a time of flight format; and
  (b) said processor responds to the operator using the input device to select two locations on the display by calculating the distance between the locations on the test part related to the two locations selected by the operator.

40. A method of analyzing and displaying ultrasonic test data obtained from a test part comprising the steps of:
  (a) storing the ultrasonic test data in a storage device;
  (b) displaying the ultrasonic test data in a format selected from the group consisting of an A-Scan, a pulse echo, a B-Scan, and a time of flight format;
  (c) selecting two locations on the display; and
  (d) determining the distance between the locations on the test part related to said two selected locations.

* * * * *

UNITED STATES PATENT AND TRADEMARK OFFICE
CERTIFICATE OF CORRECTION

PATENT NO. : 6,301,512 B1
DATED : October 9, 2001
INVENTOR(S) : W.P. Motzer

It is certified that error appears in the above-identified patent and that said Letters Patent is hereby corrected as shown below:

Title page,
Item [56] References Cited, OTHER PUBLICATIONS, " "Pseudocolo"
should read -- "Pseudocolor --

Column 14,
Line 36, "mine" should read -- mined --
Line 63, "second as of" should read -- second axis of --

Column 16,
Line 37, "and a time of flight" should read -- and time of flight --

Column 17,
Line 29, "by determine" should read -- by determining --
Line 33, "do not fill" should read -- do not fall --
Line 46, "test data in a" should read -- test data in an --

Column 18,
Line 37, "display, and" should read -- display; and --

Signed and Sealed this

Twenty-first Day of May, 2002

*Attest:*

JAMES E. ROGAN
*Attesting Officer*    *Director of the United States Patent and Trademark Office*